United States Patent [19]

Murayama et al.

[11] Patent Number: 5,284,728
[45] Date of Patent: Feb. 8, 1994

[54] ELECTROPHOTOGRAPHIC PHOTORECEPTOR CONTAINING HYDRAZONE COMPOUNDS

[75] Inventors: Tetsuo Murayama, Machida; Hitoshi Ono, Yokohama; Atsuo Saita, Machida; Sumiko Watabe, Yokohama, all of Japan

[73] Assignee: Mitsubishi Kasei Corporation, Tokyo, Japan

[21] Appl. No.: 876,085

[22] Filed: Apr. 30, 1992

[30] Foreign Application Priority Data

Apr. 30, 1991 [JP] Japan ................................ 3-99112
May 16, 1991 [JP] Japan ................................ 3-111943
Jul. 12, 1991 [JP] Japan ................................ 3-172791

[51] Int. Cl.$^5$ ................................................ G03G 5/047
[52] U.S. Cl. ............................................ 430/59; 430/73
[58] Field of Search ........................ 430/59, 73, 70, 71, 430/72, 76

[56] References Cited

U.S. PATENT DOCUMENTS

| | | | |
|---|---|---|---|
| 4,278,747 | 7/1981 | Murayama et al. | 430/82 |
| 4,367,273 | 1/1983 | Morayama et al. | 430/56 |
| 4,485,160 | 11/1984 | Suzuki et al. | 430/59 |
| 4,987,045 | 1/1991 | Suzuki et al. | 430/59 |
| 5,080,991 | 1/1992 | Ono et al. | 430/73 |
| 5,089,366 | 2/1992 | Haino et al. | 430/59 |
| 5,168,025 | 12/1992 | Ono et al. | 430/59 |

FOREIGN PATENT DOCUMENTS 0410285 1/1991 European Pat. Off. .

OTHER PUBLICATIONS

Patent Abstracts of Japan, vol. 12, No. 456(P-793){3303}, Nov. 30, 1988, & JP-A-63-178241, Jul. 22, 1988, J. Kaneko, et al., "Electrophotographic Sensitive Body".
Patent Abstracts of Japan, vol. 12, No. 146(P-206){1291}, Jun. 25, 1983, & JP-A-58-58551, Apr. 7, 1983, Y. Takei, et al., "Electrophotographic Receptor".
Patent Abstracts of Japan, vol. 10, No. 256(P-493), Sep. 2, 1986, & JP-A-61-084651, Apr. 30, 1986, H. Ueda, "Photosensitive Body".

Primary Examiner—John Goodrow
Attorney, Agent, or Firm—Oblon, Spivak, McClelland, Maier & Neustadt

[57] ABSTRACT

An electrophotographic photoreceptor comprising an electrically conductive support and a photosensitive layer formed thereon, wherein said photosensitive layer contains at least one member selected from the group consisting of hydrazone compounds of the formulas (I), (II) and (III):

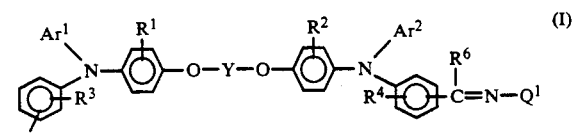

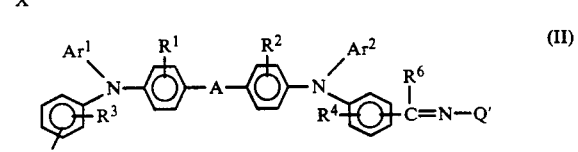

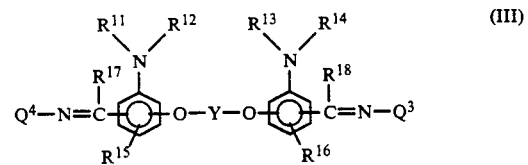

wherein X is a hydrogen atom or a group of the formula (IV):

$$-C(R^8)=N-Q^2 \qquad (IV)$$

$Q^1$ is a group of the formula (V), (VI), (VII), (VIII) or (IX); $Q^2$ is a group of the formula (VI), (VII), (VIII), (IX) or (X); each of $Q^3$ and $Q^4$ which may be the same or different, is a group of the formula (VI), (VII), (VIII), (IX) or (XI):

(Abstract continued on next page.)

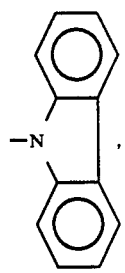 (VIII)
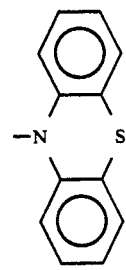 (IX)
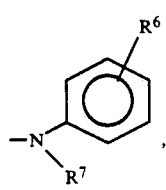 (V)
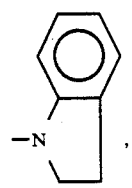 (VI)
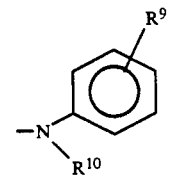 (X)
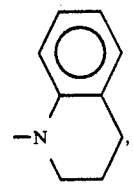 (VII)
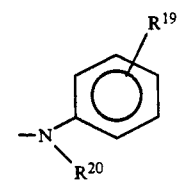 (XI)
13 Claims, 5 Drawing Sheets

ELECTROPHOTOGRAPHIC PHOTORECEPTOR CONTAINING HYDRAZONE COMPOUNDS

This invention relates to an electrophotographic photoreceptor. More particularly, it relates to a highly sensitive electrophotographic photoreceptor having a photosensitive layer comprising an organic photoconductive material.

Heretofore, inorganic photoconductive materials such as selenium, cadmium sulfide and zinc oxide have been widely used in the photosensitive layers of the electrophotographic photoreceptors. However, selenium and cadmium sulfide are required to be recovered as toxic substances. Further, selenium is crystallized by heat and thus is inferior in the heat resistance. Cadmium sulfide and zinc oxide are inferior in the moisture resistance. Zinc oxide has a drawback that it is poor in the printing resistance. Under these circumstances, research efforts are still being made to develop novel photosensitive materials. Recently, studies on use of organic photoconductive materials for the photosensitive layers of the electrophotographic photoreceptors have been advanced, and some of them have materialized into practical use. The organic photoconductive materials have many advantages over the inorganic materials. For example, they are light in weight and easy to fabricate into films, and they can be easily manufactured into photoreceptors or into transparent photoreceptors depending upon the certain kinds of the material.

Recently, the current research activities are directed to so-called function-separated photoreceptors whereby functions of generating and transporting electric charge carriers are performed by separate compounds, since they are effective for high sensitivity, and organic photoreceptors of this type have been practically employed.

As a carrier transporting material, a polymer-type photoconductive compound such as polyvinyl carbazole may be employed. Otherwise, a low molecular weight photoconductive compound may be used as dispersed or dissolved in a binder polymer.

Particularly in the case of an organic low molecular weight photoconductive compound, it is possible to select as a binder a polymer excellent in the film-forming property, flexibility and adhesive property, whereby a photoreceptor excellent in the mechanical properties can readily be obtained (e.g. Japanese Unexamined Patent Publications No. 196767/1985, No. 218652/1985, No. 233156/1985, No. 48552/1988 and No. 267552/1989). However, it has been difficult to find a suitable compound for the preparation of a highly sensitive photoreceptor.

The present inventors have conducted extensive researches for organic low molecular weight photoconductive compounds capable of presenting electrophotographic photoreceptors having high sensitivity and high durability and as a result, have found that certain specific hydrazone compounds are suitable for this purpose. The present invention has been accomplished on the basis of this discovery.

Thus, the present invention provides an electrophotographic photoreceptor comprising an electrically conductive support and a photosensitive layer formed thereon, wherein said photosensitive layer contains at least one member selected from the group consisting of hydrazone compounds of the formulas (I), (II) and (III):

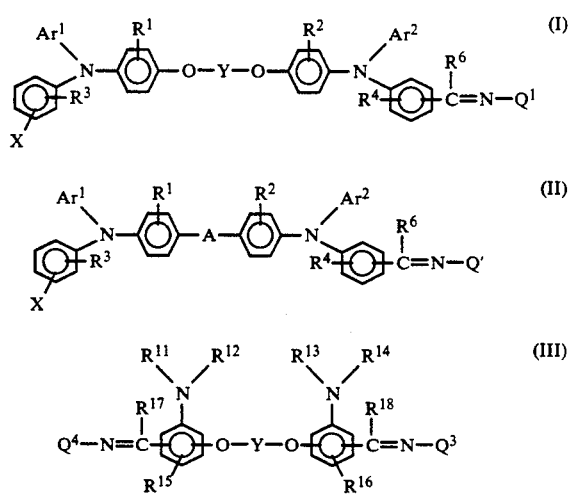

wherein X is a hydrogen atom or a group of the formula (IV):

$$-C(R^8)=N-Q^2 \qquad (IV)$$

$Q^1$ is a group of the formula (V), (VI), (VII), (VIII) or (IX); $Q^2$ is a group of the formula (VI), (VII), (VIII), (IX) or (X); each of $Q^3$ and $Q^4$ which may be the same or different, is a group of the formula (VI), (VII), (VIII), (IX) or (XI):

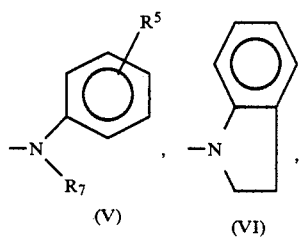

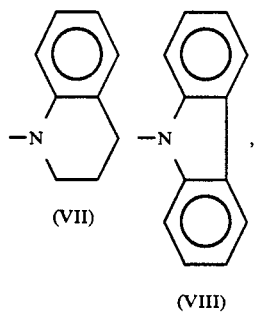

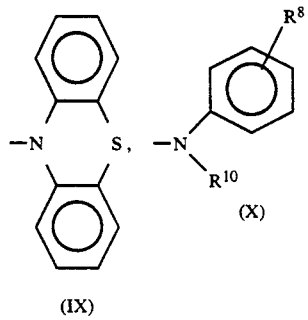

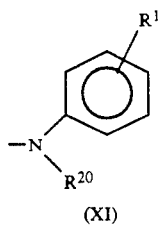

(XI)

Y is a bivalent hydrocarbon group which may have substituents, A is an aliphatic linking group which may have substituents, where the main chain of the linking group may contain an oxygen atom or a carbon-carbon double bond; in the case where the main chain of the linking group is composed of only carbon atoms, the constituting carbon number is from 3 to 5; and in the case where the oxygen atom is contained, the constituting carbon-carbon chain length has the carbon number of from 2 to 5; each of $Ar^1$ and $Ar^2$ which may be the same or different, is an aryl group which may have substituents or a heterocyclic group; each of $R^1$, $R^2$, $R^3$, $R^4$, $R^5$, $R^9$, $R^{15}$, $R^{16}$ and $R^{19}$ which may be the same or different, is a hydrogen atom, a lower alkyl group which may have substituents, a halogen atom or a lower alkoxy group which may have substituents; each of $R^6$, $R^8$, $R^{17}$ and $R^{18}$ which may be the same or different, is a hydrogen atom, a methyl group or a phenyl group which may have substituents; each of $R^7$ and $R^{10}$ is an aryl group which may have substituents in the formula (I), or an aryl group which may have substituents or a heterocyclic group in the formula (II); each of $R^{11}$, $R^{12}$, $R^{13}$ and $R^{14}$ which may be the same or different, is an alkyl group which may have substituents, an aralkyl group which may have substituents; an aryl group which may have substituents, a vinyl group which may have substituents, or an allyl group; and $R^{20}$ is an aryl group which may have substituents; or a heterocyclic group.

In the accompanying drawings, FIG. 1 is an infrared absorption spectrum of the monohydrazone compound obtained in Preparation Example 2.

Figure 1:
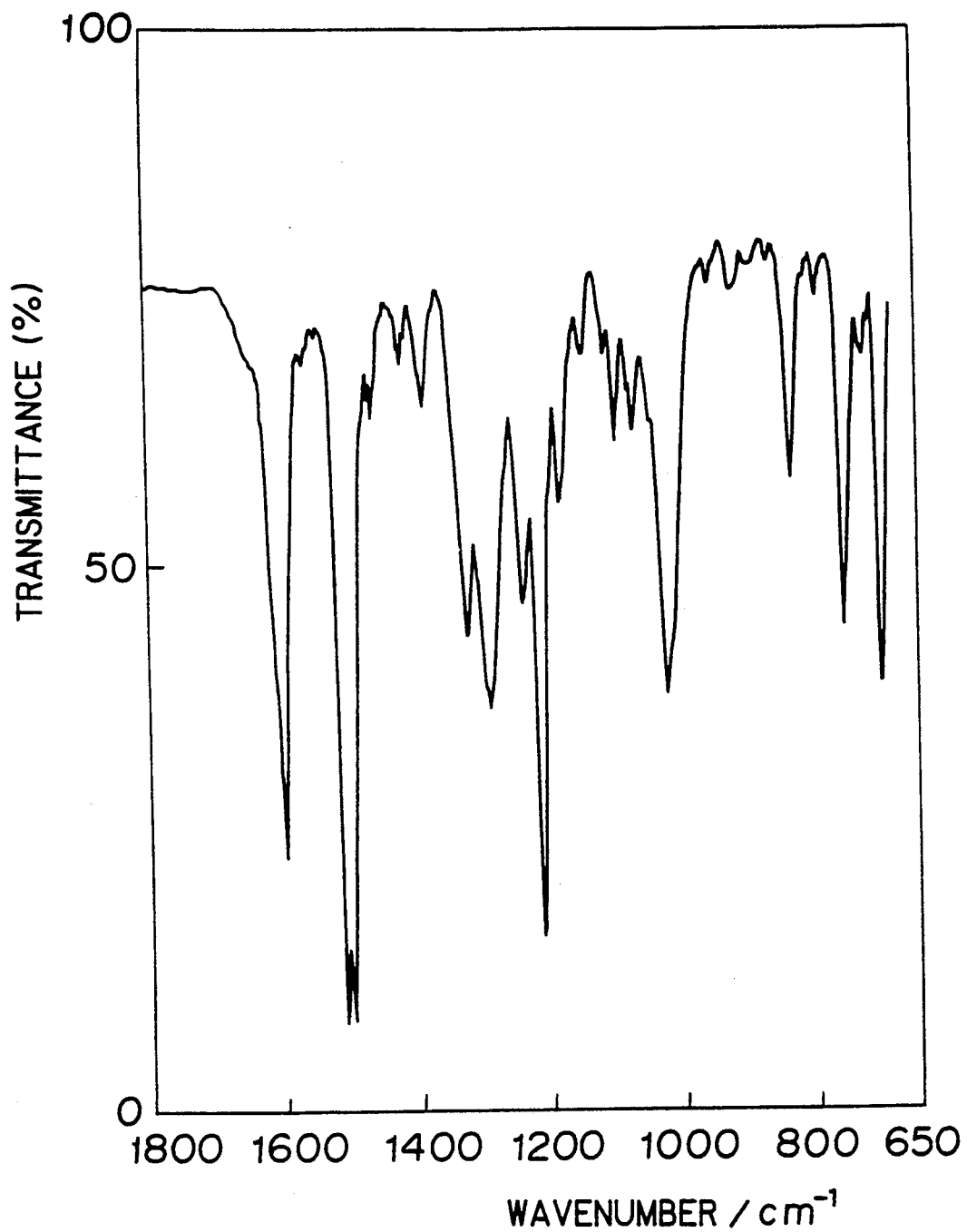

Now, the present invention will be described in detail with reference to the preferred embodiments.

The electrophotographic photoreceptor of the present invention contains at least one member selected from the group consisting of hydrazone compounds of the formulas (I), (II) and (III) in the photosensitive layer.

In the formula (I), (II) or (III), X is an hydrogen atom or a group of the formula (IV):

$$-C(R^8)=N-Q^2 \quad \text{(IV)}$$

$Q^1$ is a group of the formula (V), (VI), (VII), (VIII) or (IX); $Q^2$ is a group of the formula (VI), (VII), (VIII), (IX) or (X); each of $Q^3$ and $Q^4$ which may be the same or different, is a group of the formula (VI), (VII), (VIII), (IX) or (XI):

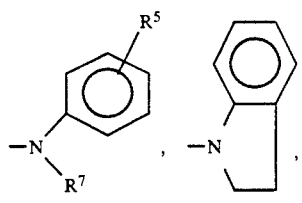

(V)   (VI)

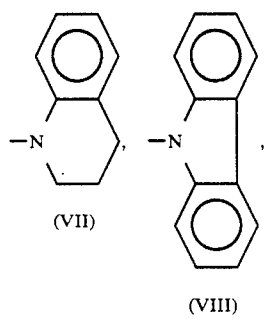

(VII)

(VIII)

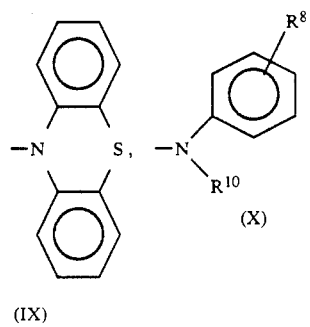

(IX)   (X)

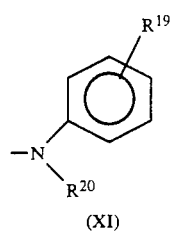

(XI)

Y is a bivalent hydrocarbon group, for example, a methylene group, a propylene group, a xylylene group, a cyclohexylene group, a vinylene group or a phenylene group which may have substituents such as a halogen atom, a hydroxyl atom, a saturated or unsaturated hydrocarbon group, an alkoxy group, an aryloxy group, a dialkylamino group or a diarylamino group.

A is an aliphatic linking group which may have substituents, for example, a lower alkyl group such as a methyl group or an ethyl group, a lower alkoxy group such as a methoxy group or an ethoxy group, a halogen atom such as a chlorine atom or a bromine atom or an aryl group such as a phenyl group or a naphthyl group. In the case where the main chain of the linking group is composed of only carbon atoms, the constituting carbon number is preferably from 3 to 5 in view of the improvement of solubility in a solvent.

In the case where the main chain of the linking group contains the oxygen atom, the main chain has the form of an ether linkage and the constituting carbon-carbon chain length has the carbon number of from 2 to 5.

Each of $Ar^1$ and $Ar^2$ which may be the same or different, is an aryl group such as a phenyl group or a naphthyl group which may be substituted by a lower alkyl group such as a methyl group or an ethyl group, a lower alkoxy group such as a methoxy group or an ethoxy group or a phenyl group; or a heterocyclic group such as a pyrrolyl group, a thiophenyl group, a furyl group or a carbazolyl group which may be substituted by the same substituents as the above.

Each of $R^1$, $R^2$, $R^3$, $R^4$, $R^5$, $R^9$, $R^{15}$, $R^{16}$ and $R^{19}$ which may be the same or different, is a hydrogen atom; a halogen atom such as a chlorine atom, a bromine atom or an iodine atom; a lower alkyl group such as a methyl group or an ethyl group; or a lower alkoxy group such as a methoxy group or an ethoxy group. Each of the lower alkyl group and the lower alkoxy group may have substituents.

Each of $R^6$, $R^8$, $R^{17}$ and $R^{18}$ which may be the same or different, is a hydrogen atom; a methyl group; a phenyl group; or a substituted phenyl group such as a tolyl group, an anisyl group or a chlorophenyl group.

In the formula (I), each of $R^7$ and $R^{10}$ which may be the same or different, is a phenyl group; or an aryl group which may have substituents, such as a tolyl group, an anisyl group or a chlorophenyl group.

In the formula (II), each of $R^7$ and $R^{10}$ which may be the same or different, is a phenyl group; an aryl group which may have substituents, such as a tolyl group, an anisyl group or a chlorophenyl group; or a heterocyclic group such as a pyrrolyl group, a thiophenyl group, a furyl group or a carbazolyl group.

Each of $R^{11}$, $R^{12}$, $R^{13}$ and $R^{14}$ which may be the same or different, is an alkyl group such as a methyl group, an ethyl group, a propyl group, a butyl group or a hexyl group; an aralkyl group such as a benzyl group, a naphthylmethyl group or a phenethyl group; an aryl group such as a phenyl group or a naphthyl group; a vinyl group; or an allyl group. Each of the alkyl group, the aralkyl group, the aryl group and the vinyl group may be substituted with a lower alkyl group such as a methyl group or an ethyl group, a lower alkoxy group such as a methoxy group or an ethoxy group, or a phenyl group.

$R^{20}$ is a phenyl group; an aryl group which may have substituents, such as a tolyl group, an anisyl group or a chlorophenyl group; or a heterocyclic group such as a pyrrolyl group, a thiophenyl group, a furyl group or a carbazolyl group.

Typical examples of the arylamine hydrazone compound of the formula (I) are given hereinbelow. However, the arylamine hydrazone compound useful in the present invention is by no means limited to the typical examples so long as it does not exceed the gist of the present invention.

Exemplary Compounds of arylamine hydrazone compound of the formula (I)

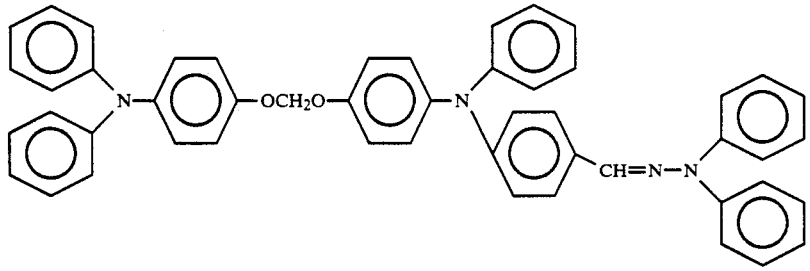

(1-1)

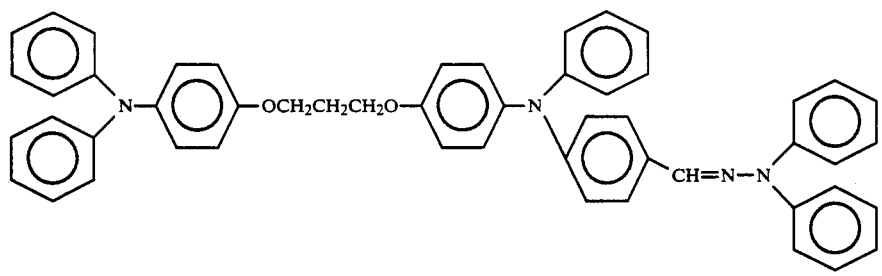

(1-2)

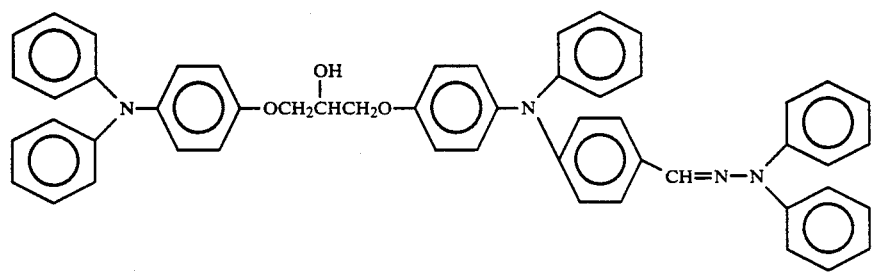

(1-3)

-continued
Exemplary Compounds of arylamine hydrazone compound of the formula (I)
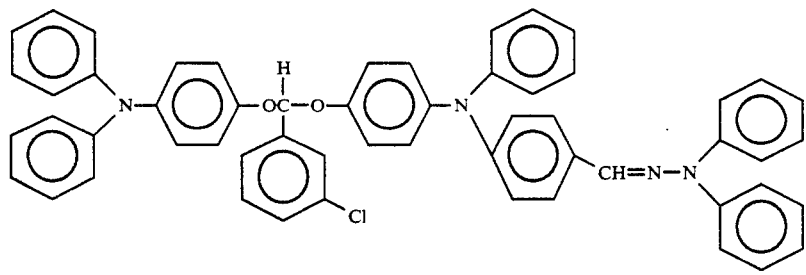
(1-4)
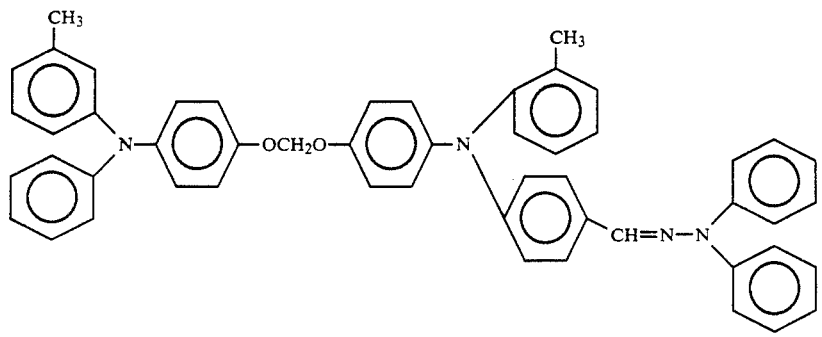
(1-5)
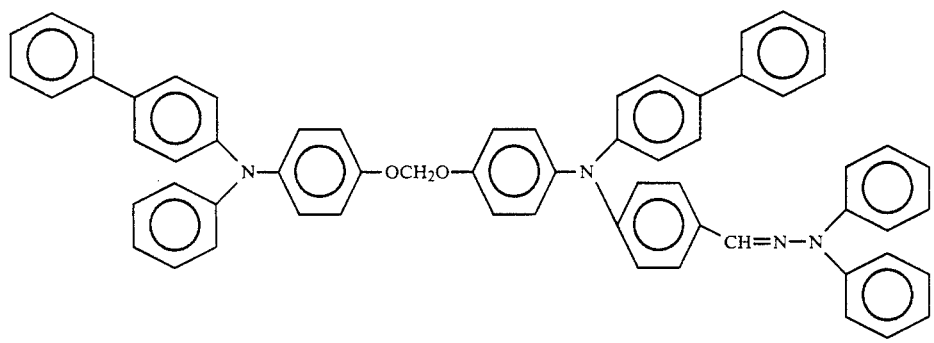
(1-6)
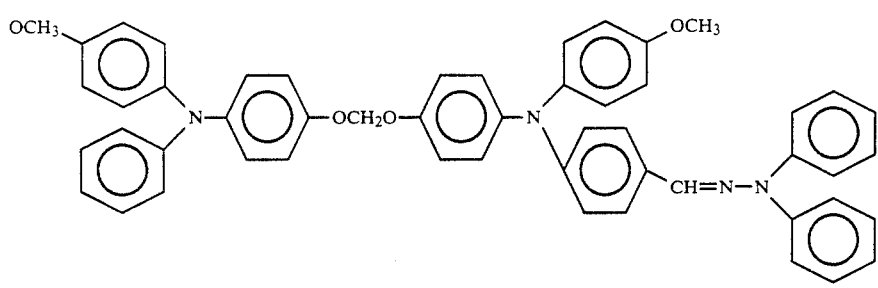
(1-7)
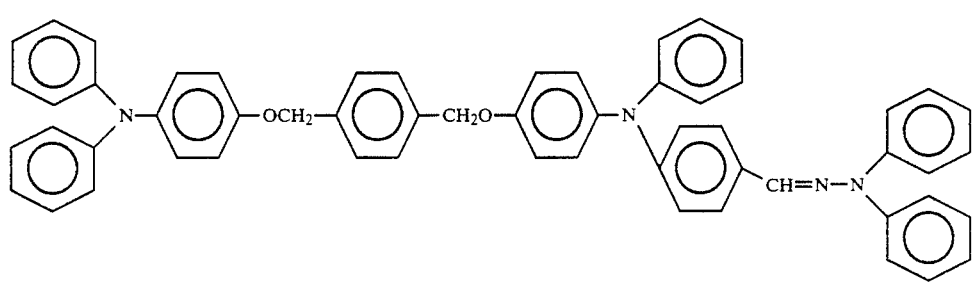
(1-8)

-continued
Exemplary Compounds of arylamine hydrazone compound of the formula (I)
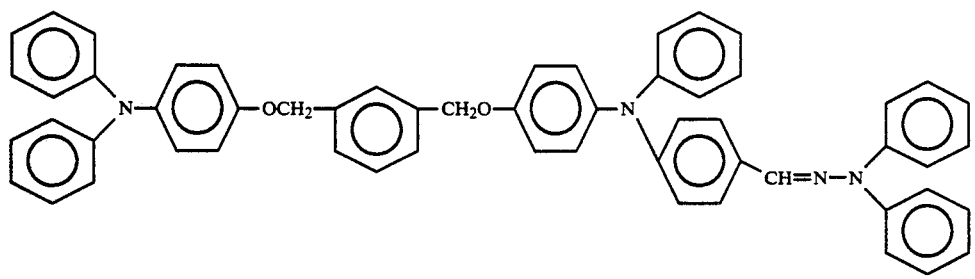
(1-9)
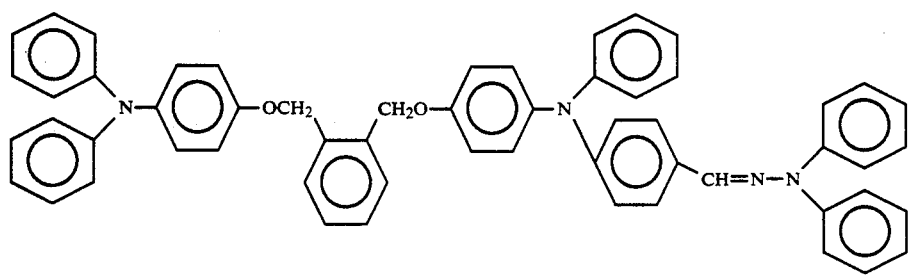
(1-10)
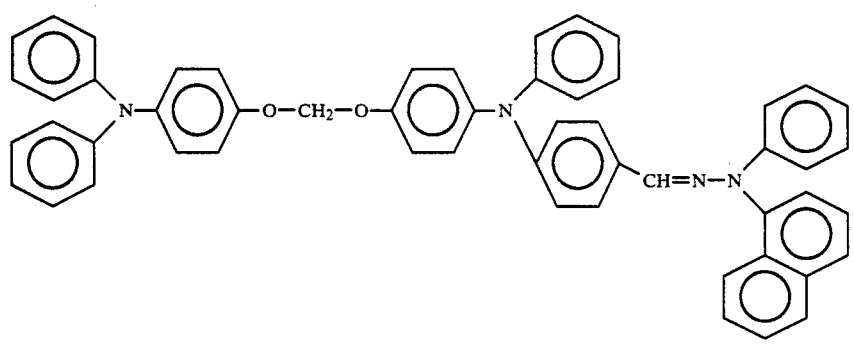
(1-11)
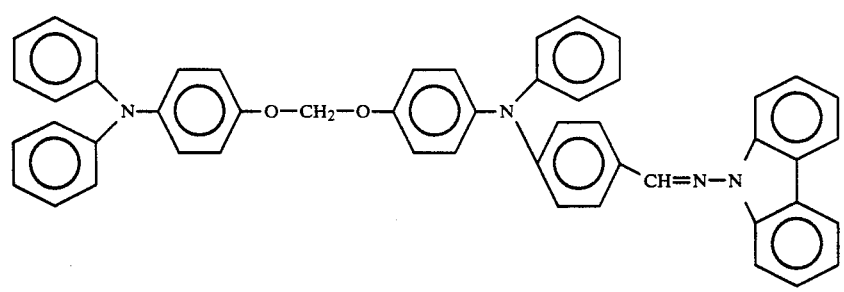
(1-12)
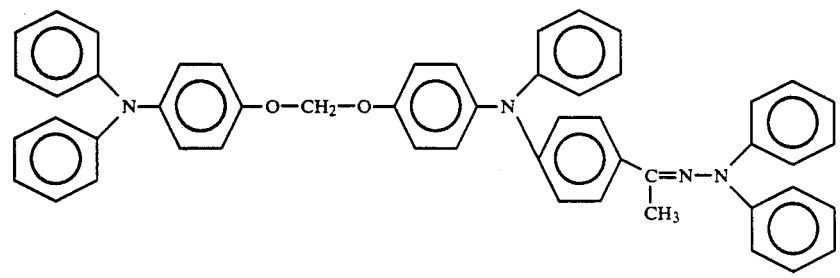
(1-13)

-continued
Exemplary Compounds of arylamine hydrazone compound of the formula (I)
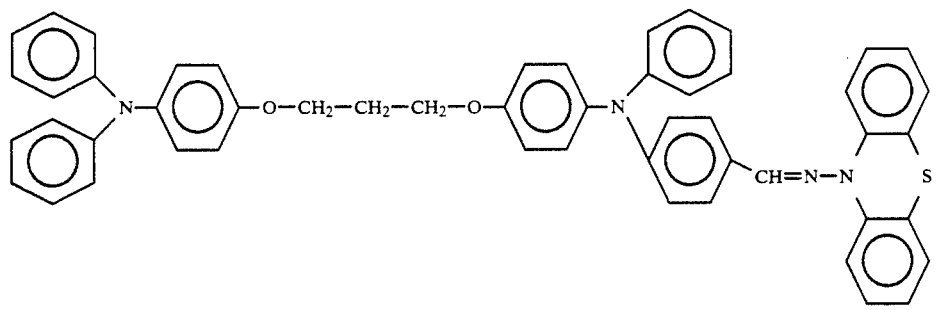
(1-14)
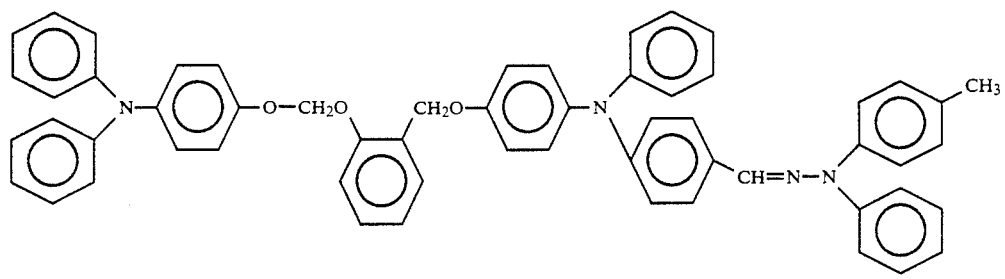
(1-15)
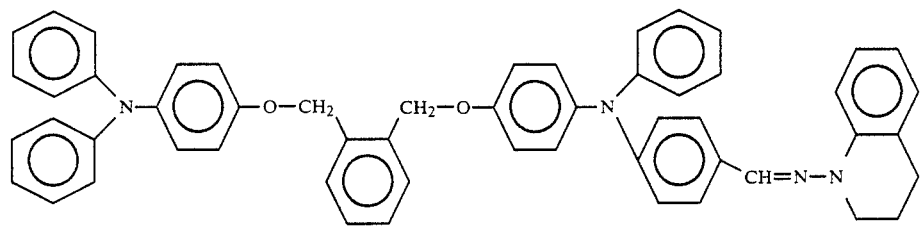
(1-16)
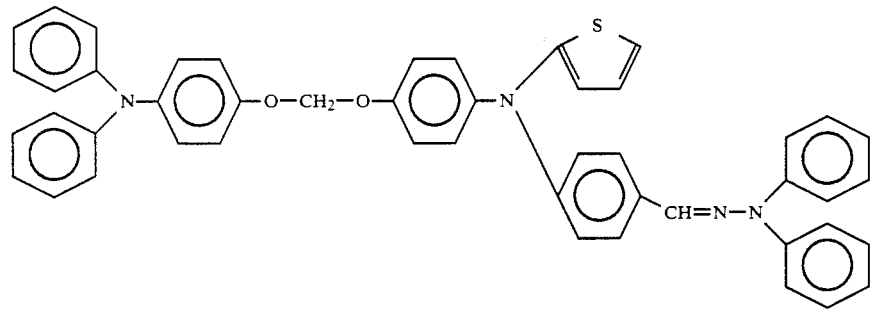
(1-17)
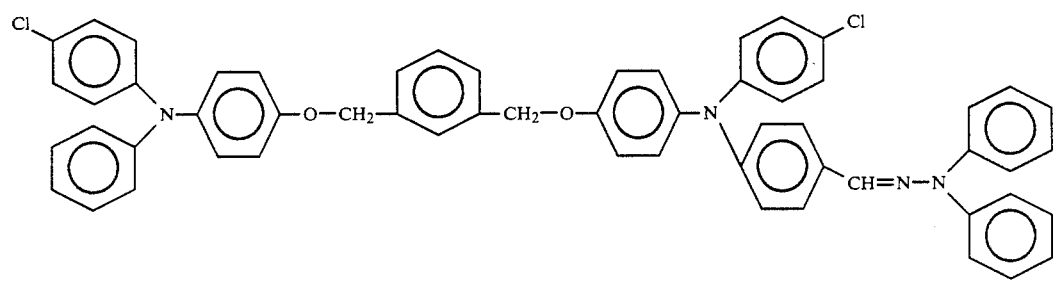
(1-18)

-continued
Exemplary Compounds of arylamine hydrazone compound of the formula (I)
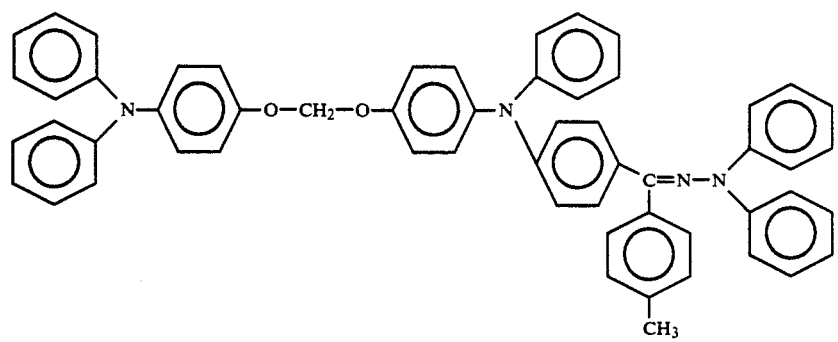
(1-19)
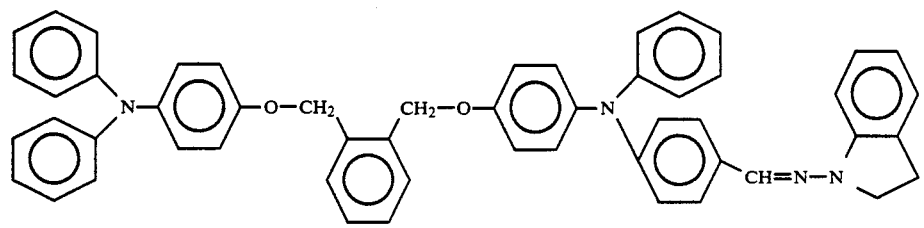
(1-20)
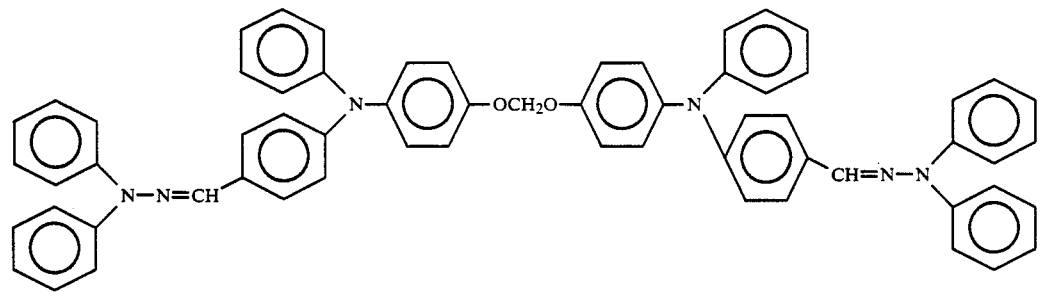
(1-21)
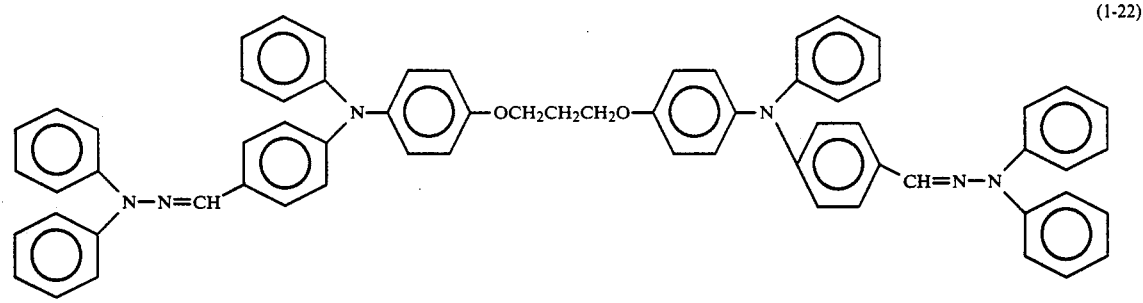
(1-22)
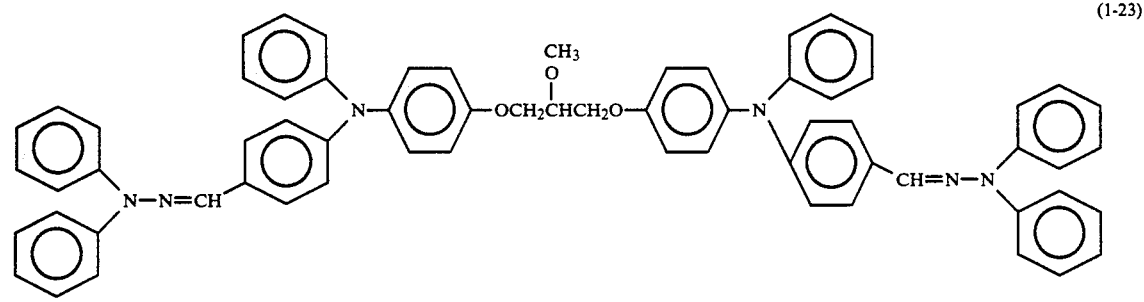
(1-23)

Exemplary Compounds of arylamine hydrazone compound of the formula (I)
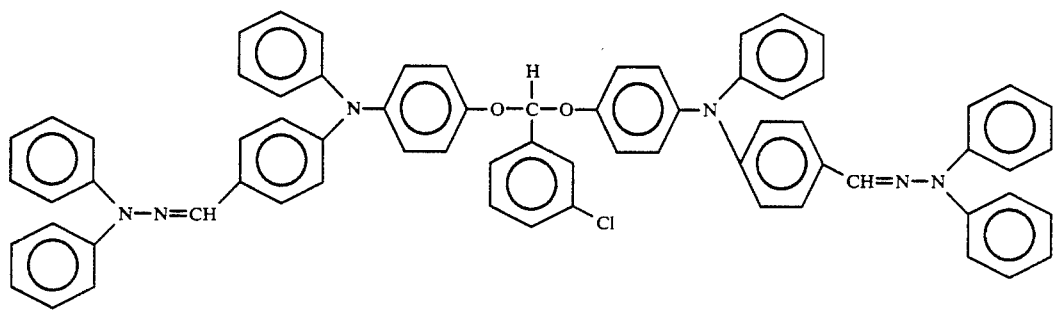
(1-24)
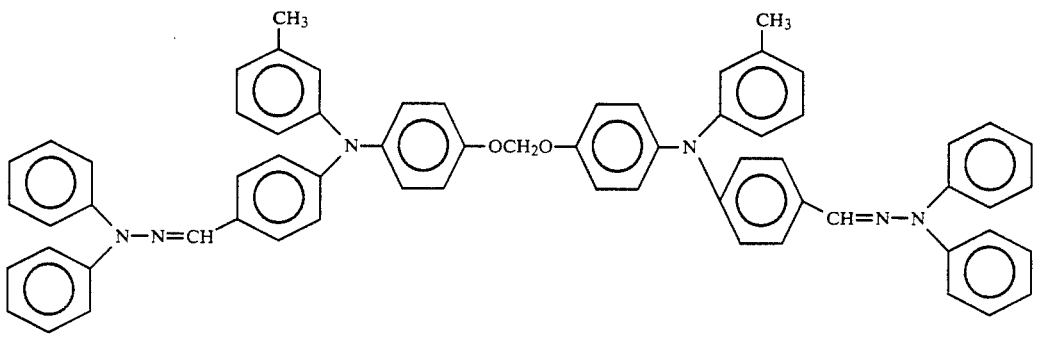
(1-25)
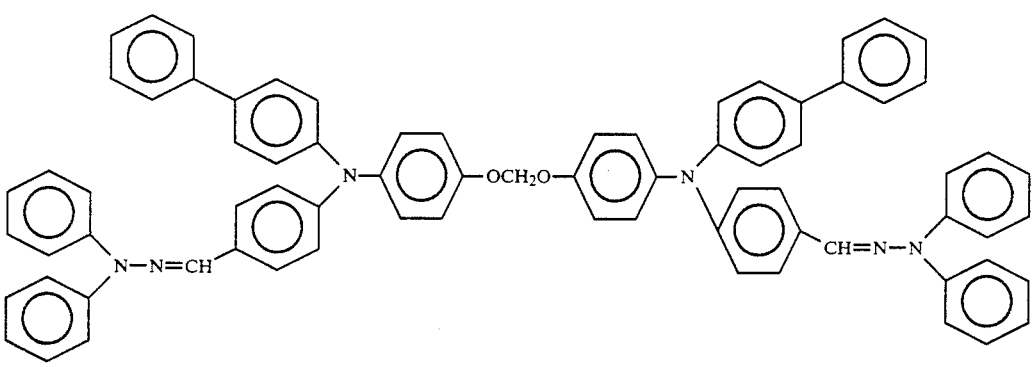
(1-26)
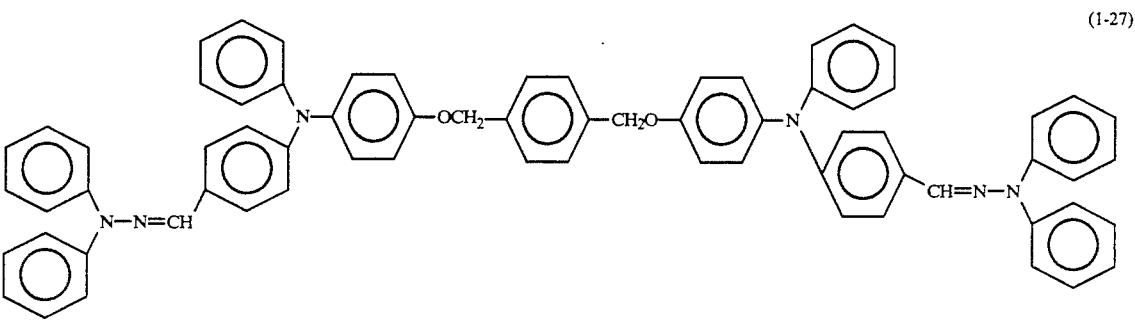
(1-27)

-continued
Exemplary Compounds of arylamine hydrazone compound of the formula (I)
(1-28)
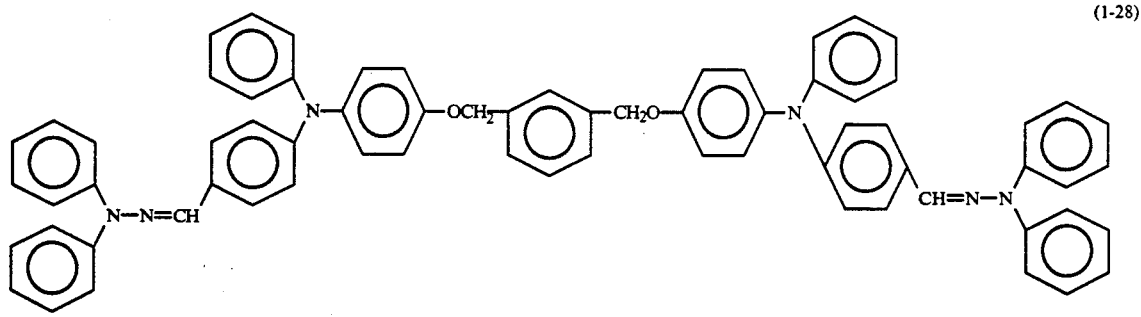
(1-29)
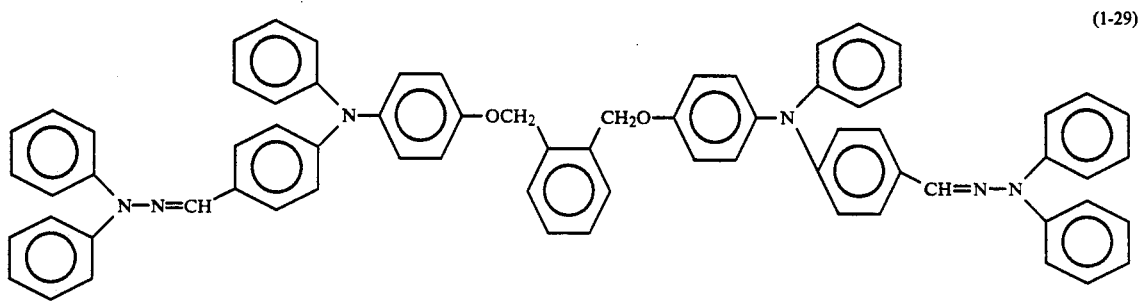
(1-30)
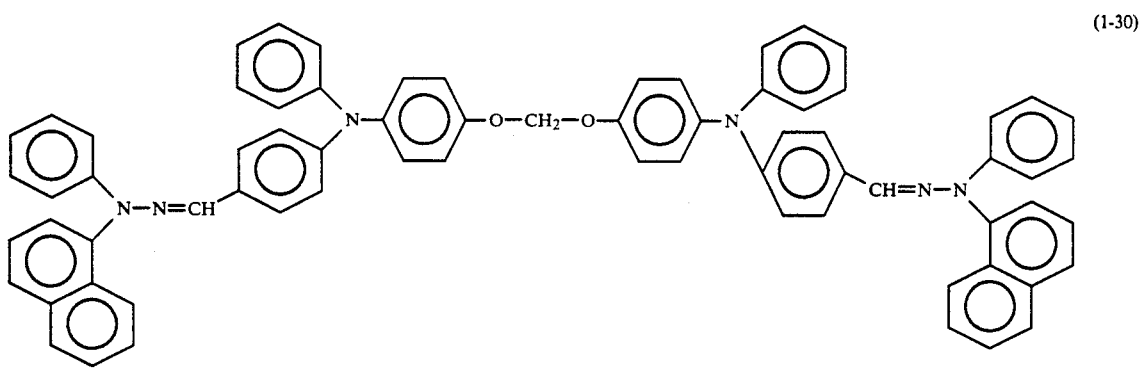
(1-31)
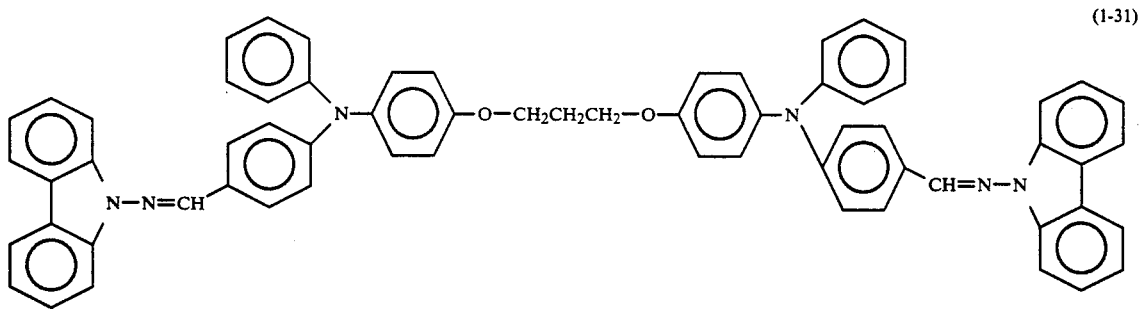
(1-32)
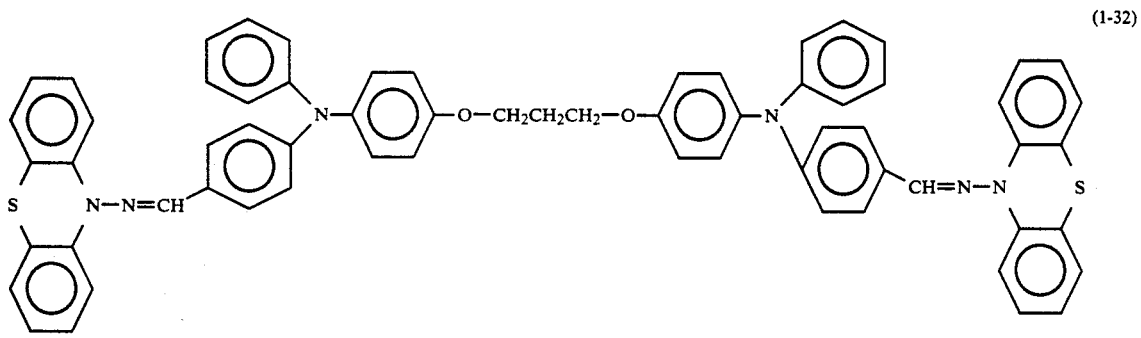

-continued
Exemplary Compounds of arylamine hydrazone compound of the formula (I)
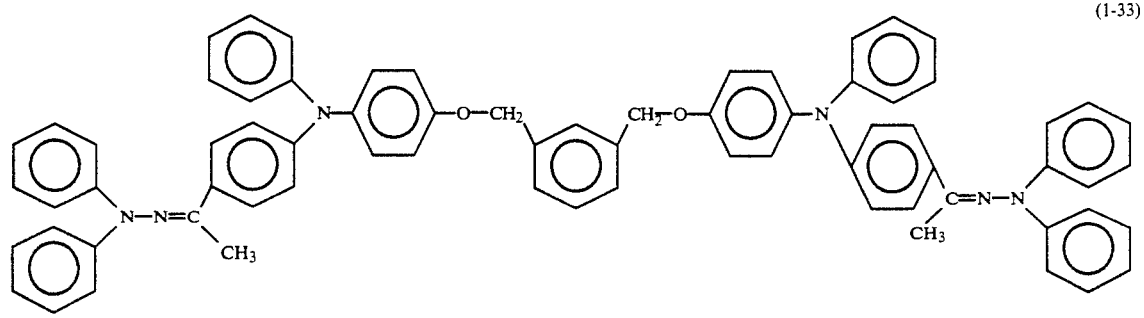
(1-33)
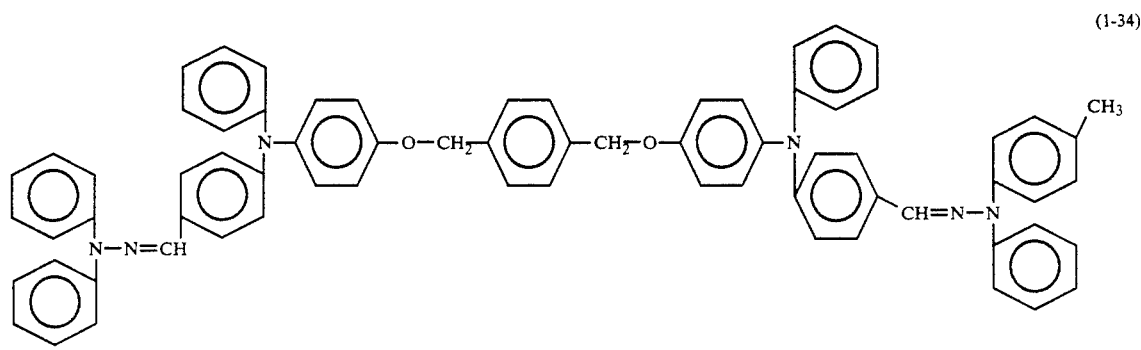
(1-34)
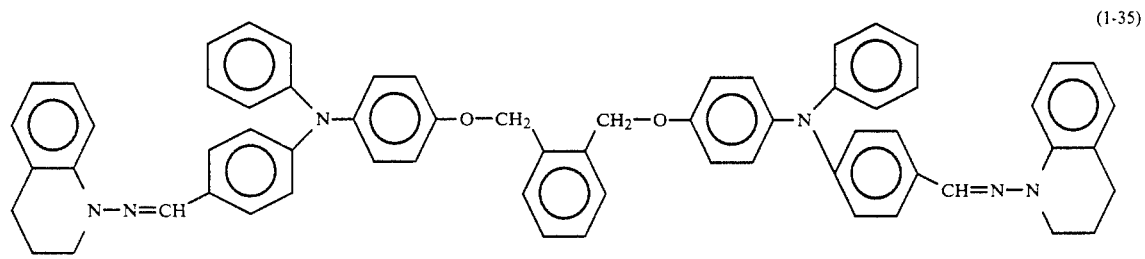
(1-35)
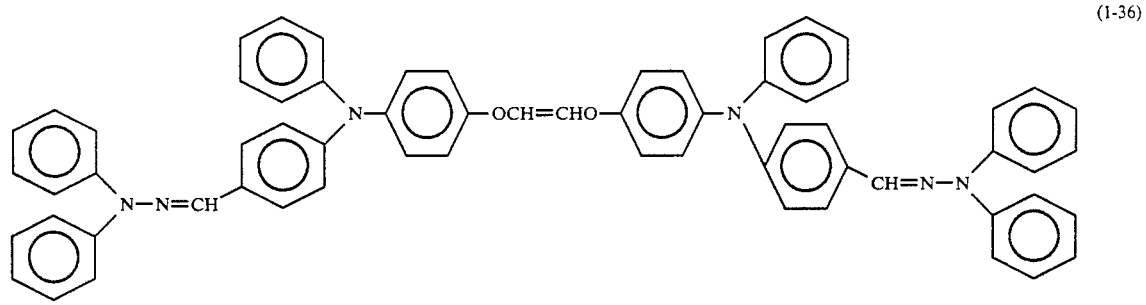
(1-36)
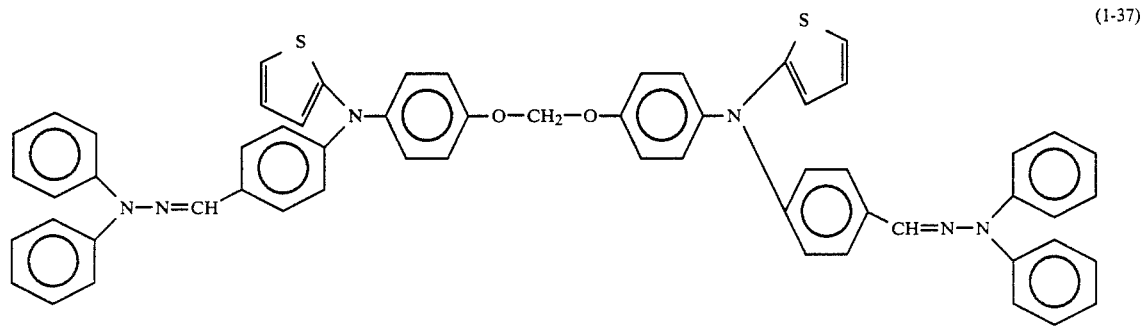
(1-37)

-continued

Exemplary Compounds of arylamine hydrazone compound of the formula (I)

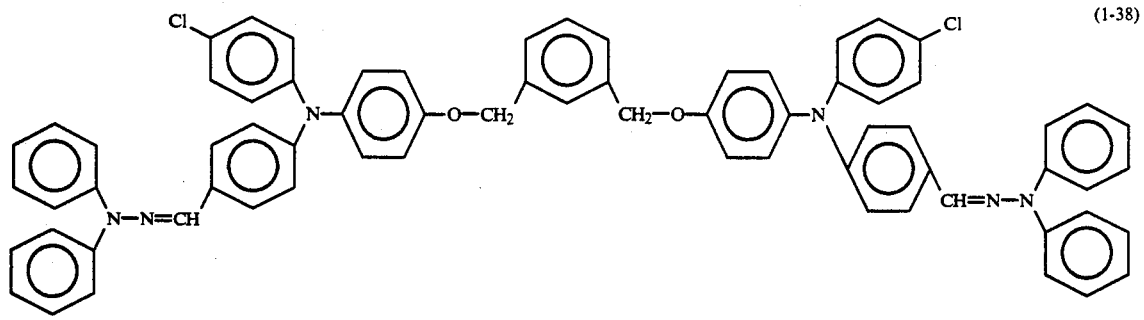
(1-38)

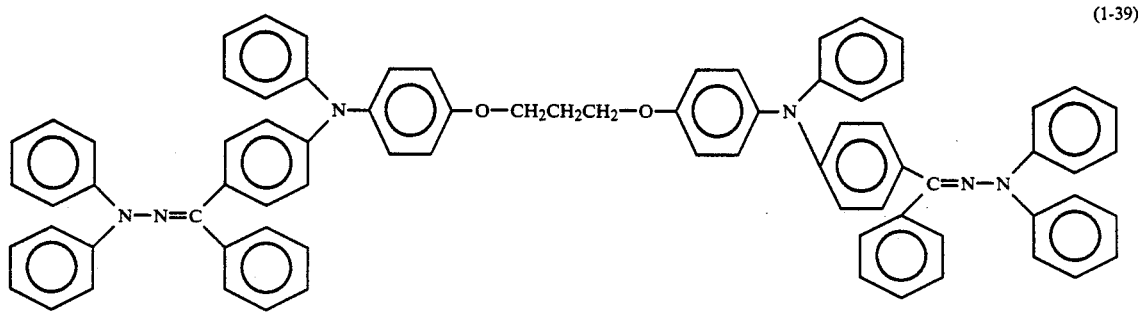
(1-39)

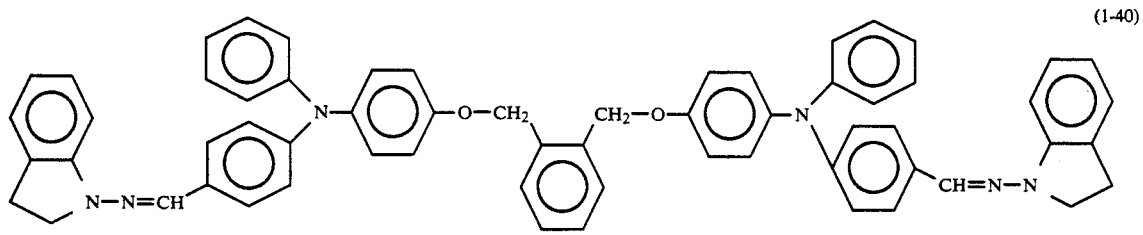
(1-40)

Typical examples of the the arylamine hydrazone compound of the formula (II) are given hereinafter. However, the arylamine hydrazone compound useful in the present invention is by no means limited to these typical examples so long as it does not exceed the gist of the present invention.

Exemplary Compounds of arylamine hydrazone compound of the formula (II)

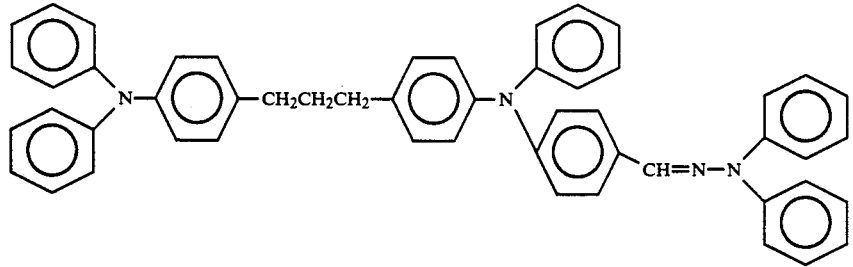
(2-1)

-continued
Exemplary Compounds of arylamine hydrazone compound of the formula (II)
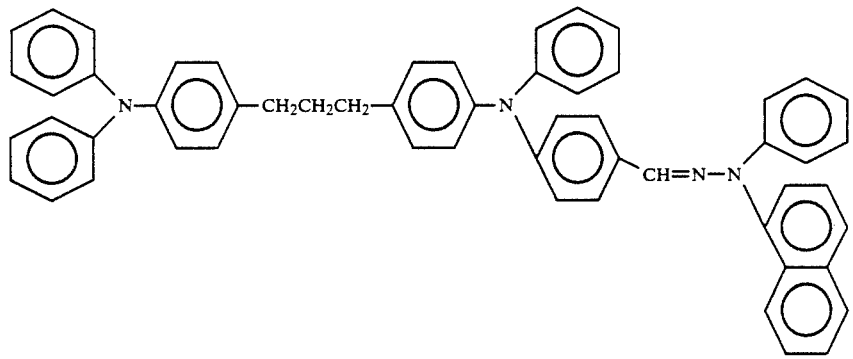
(2-2)
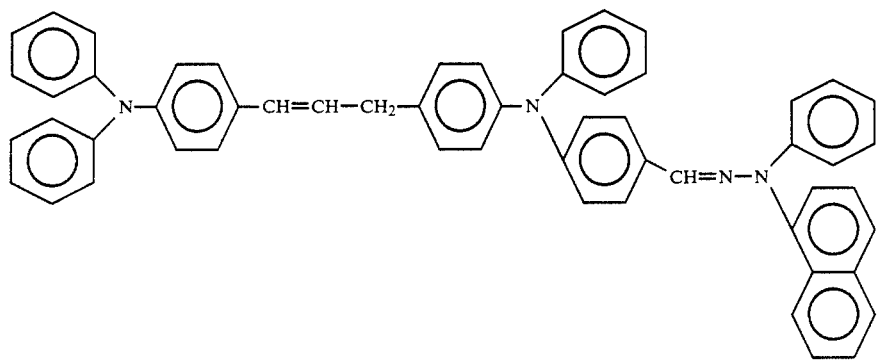
(2-3)
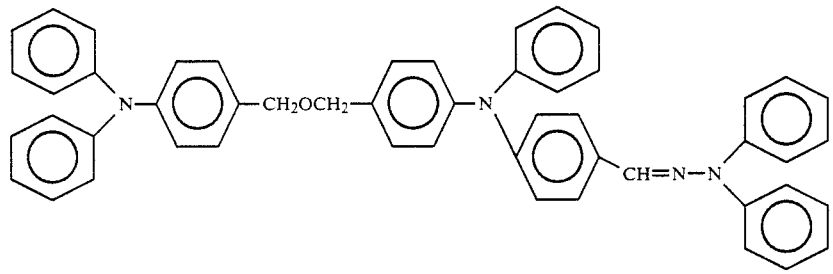
(2-4)
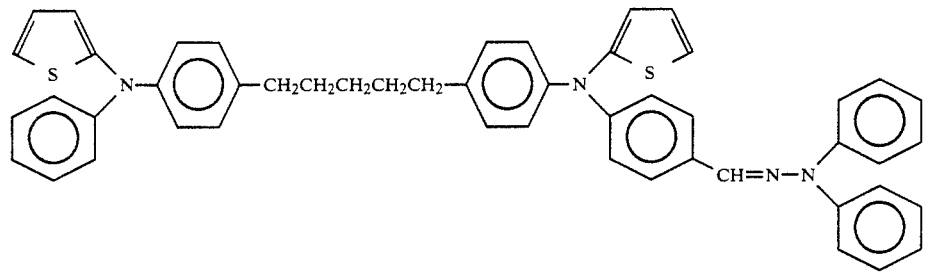
(2-5)
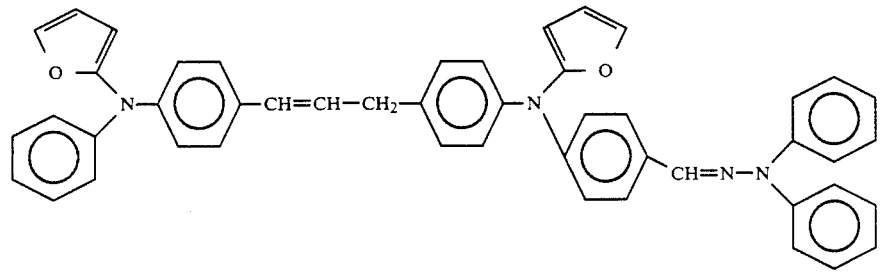
(2-6)

-continued
Exemplary Compounds of arylamine hydrazone compound of the formula (II)
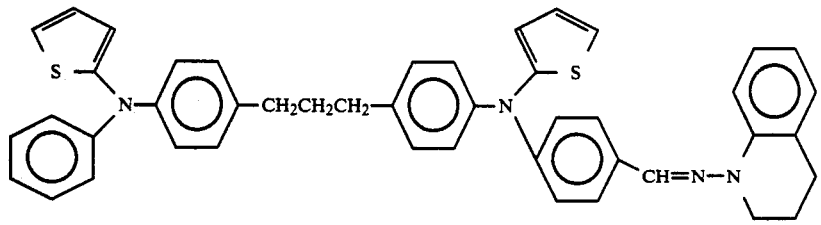
(2-7)
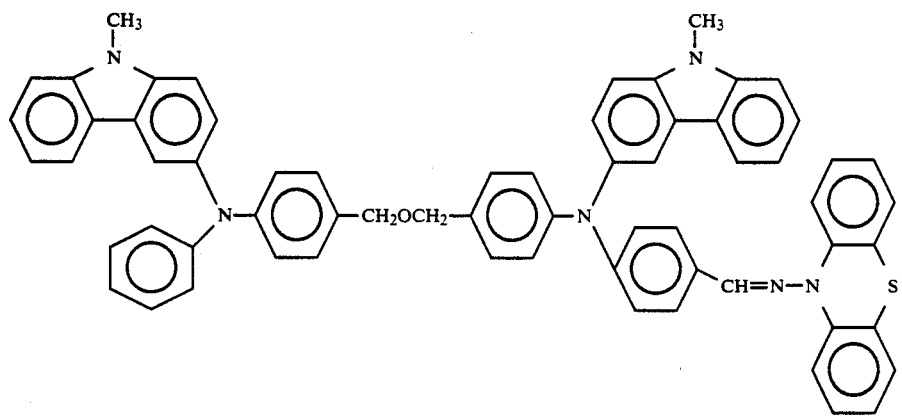
(2-8)
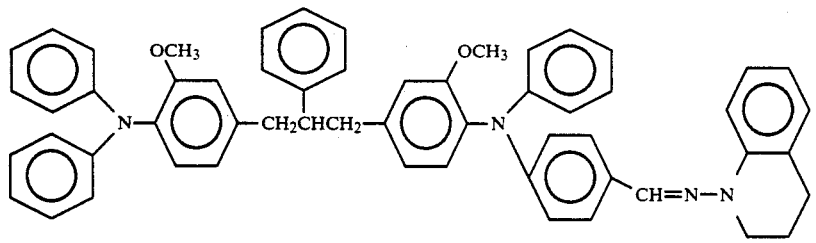
(2-9)
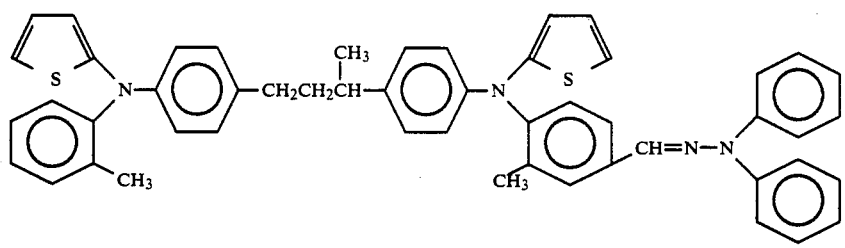
(2-10)
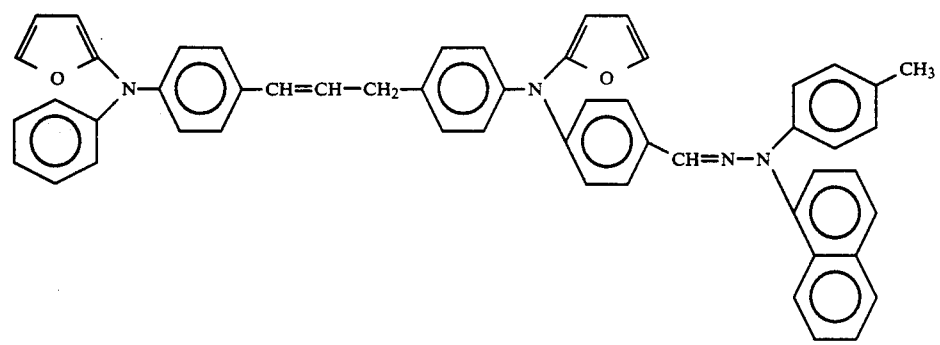
(2-11)

-continued
Exemplary Compounds of arylamine hydrazone compound of the formula (II)
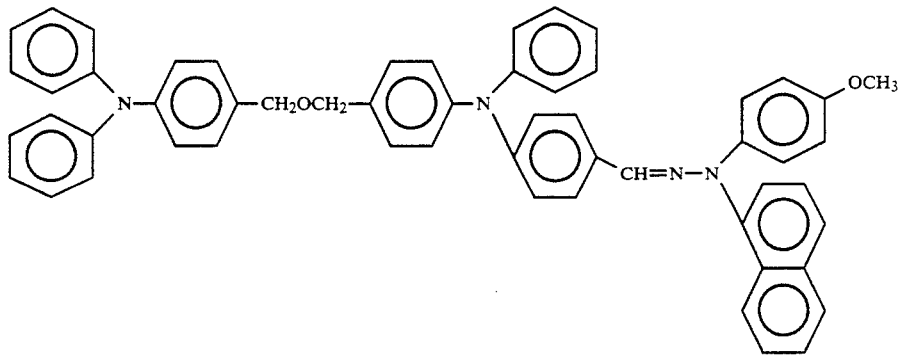
(2-12)
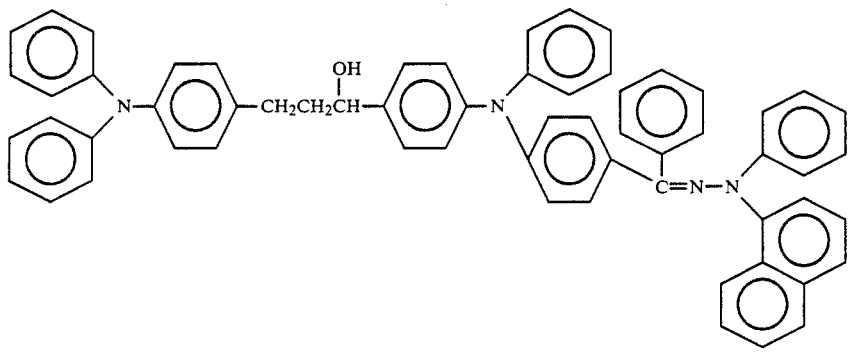
(2-13)
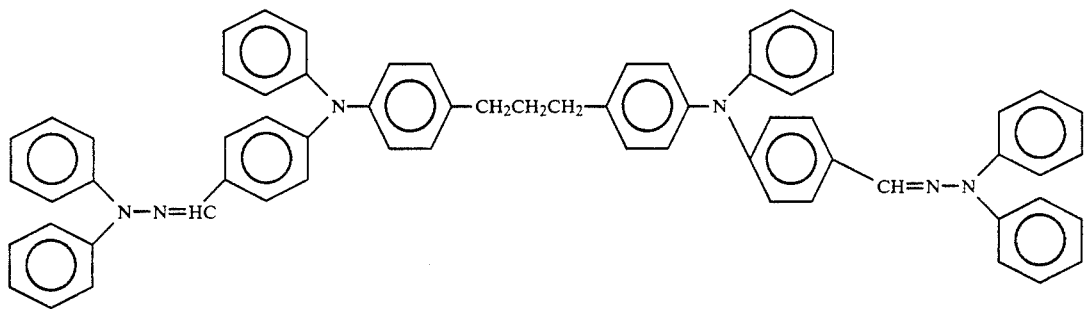
(2-14)
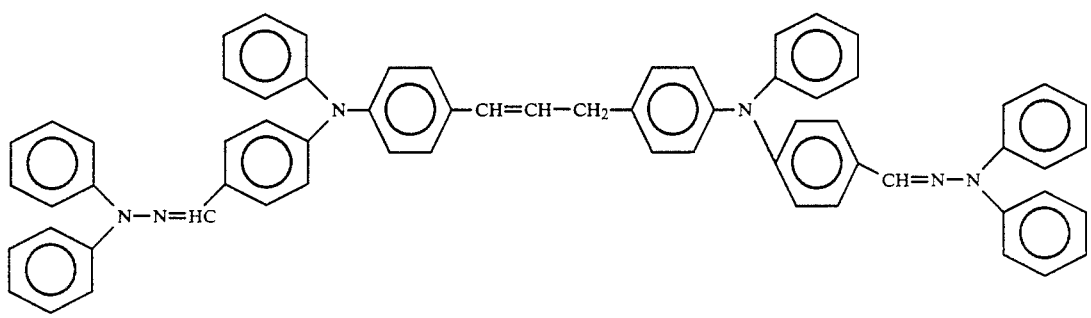
(2-15)

-continued
Exemplary Compounds of arylamine hydrazone compound of the formula (II)
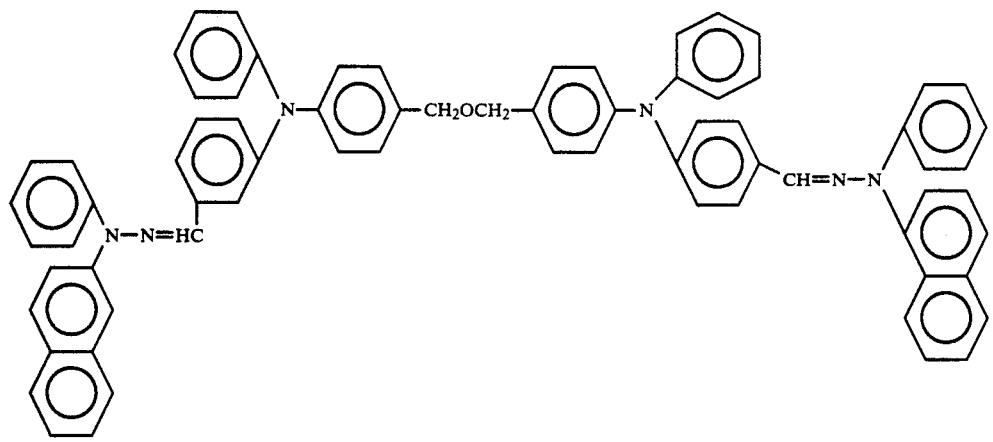
(2-16)
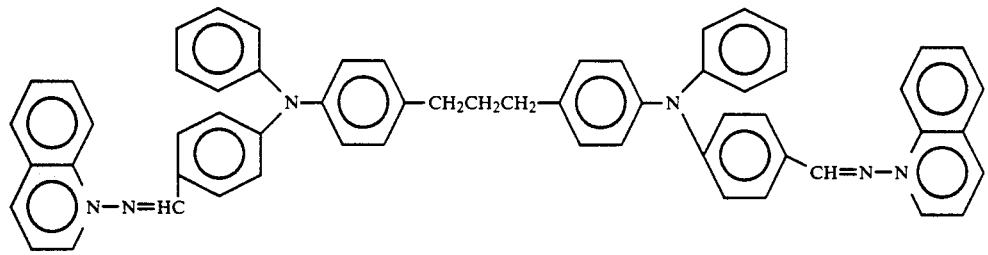
(2-17)
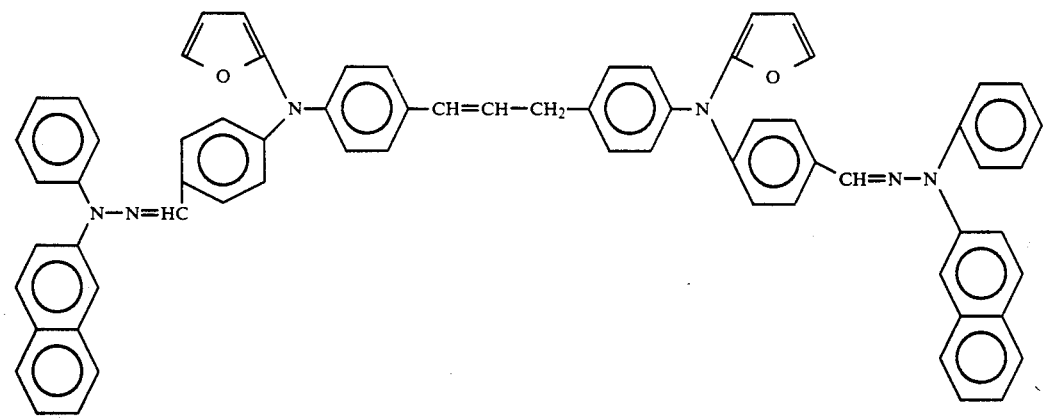
(2-18)
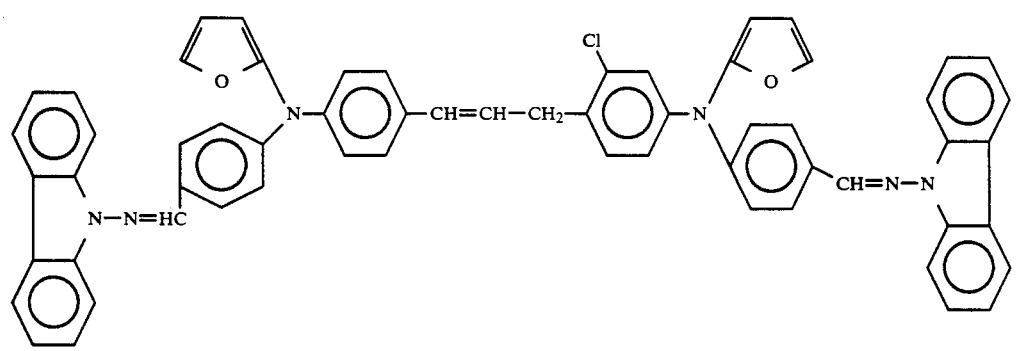
(2-19)

-continued
Exemplary Compounds of arylamine hydrazone compound of the formula (II)
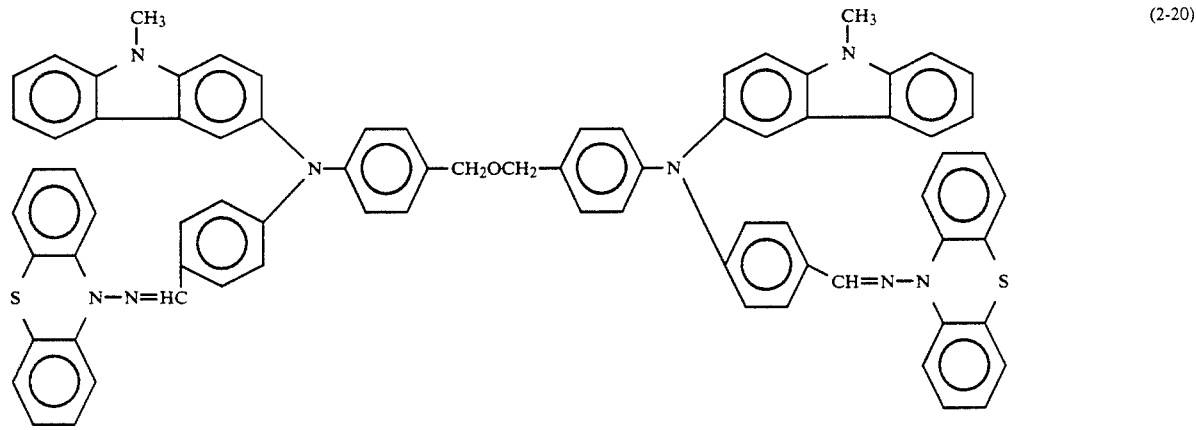
(2-20)
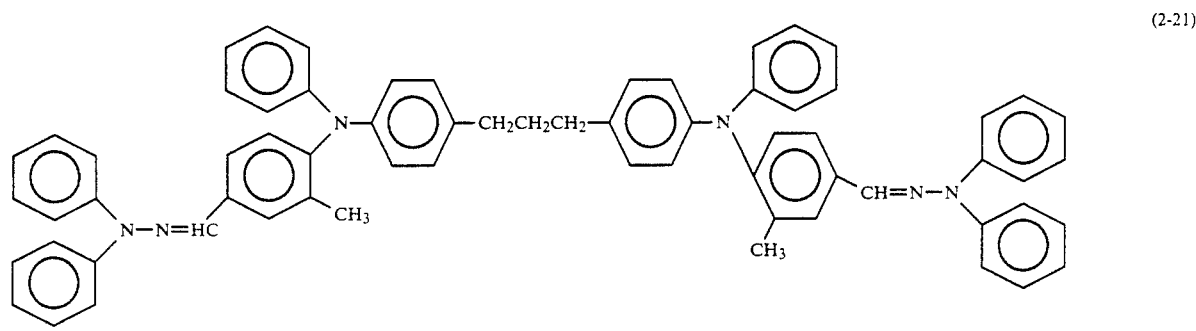
(2-21)
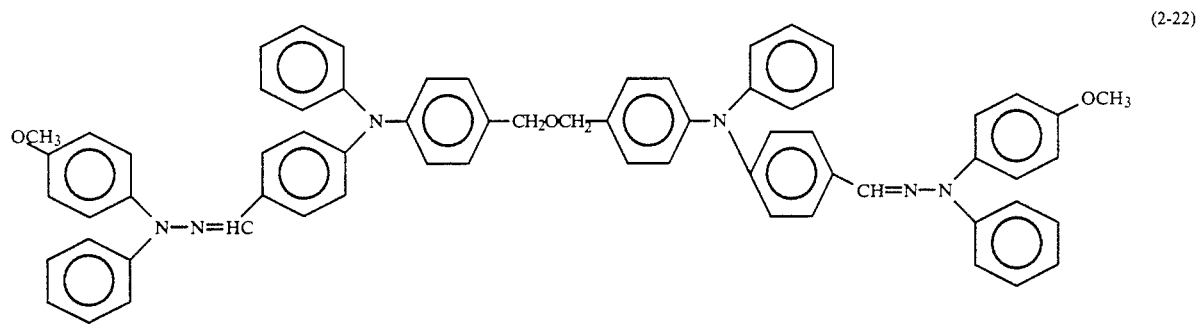
(2-22)
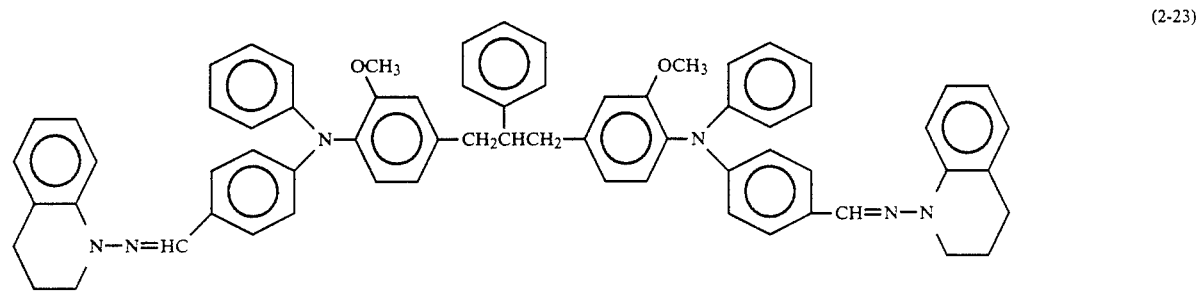
(2-23)

-continued
Exemplary Compounds of arylamine hydrazone compound of the formula (II)
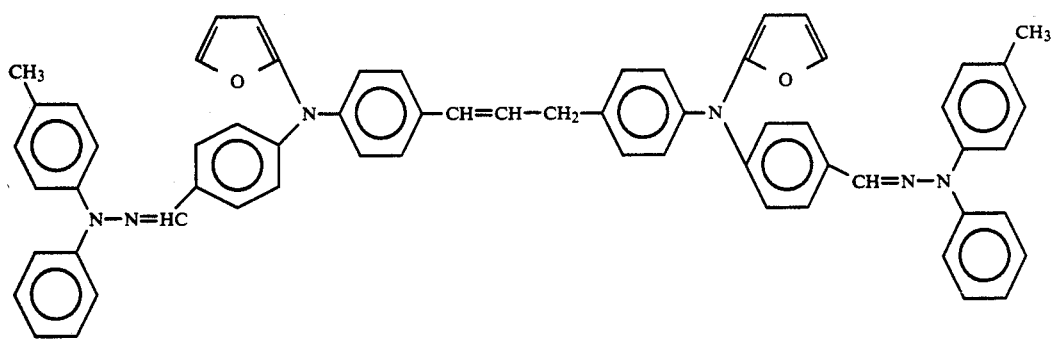
(2-24)
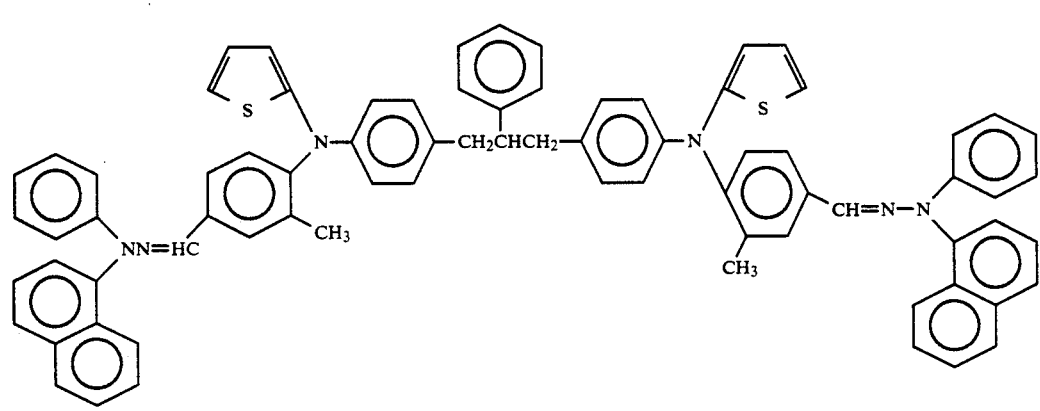
(2-25)
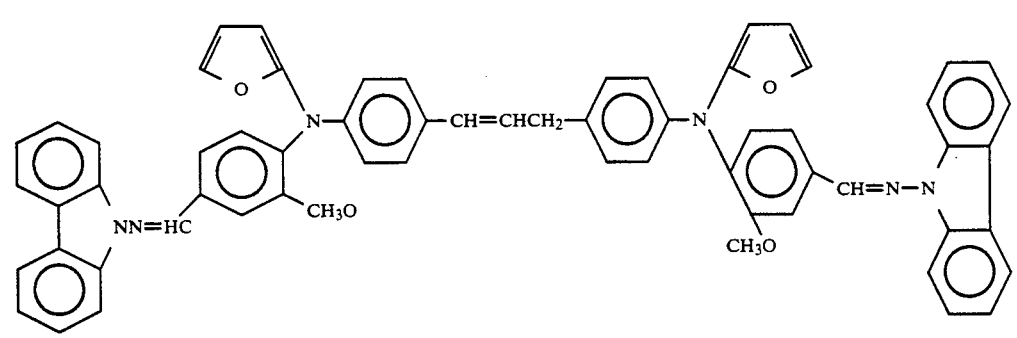
(2-26)
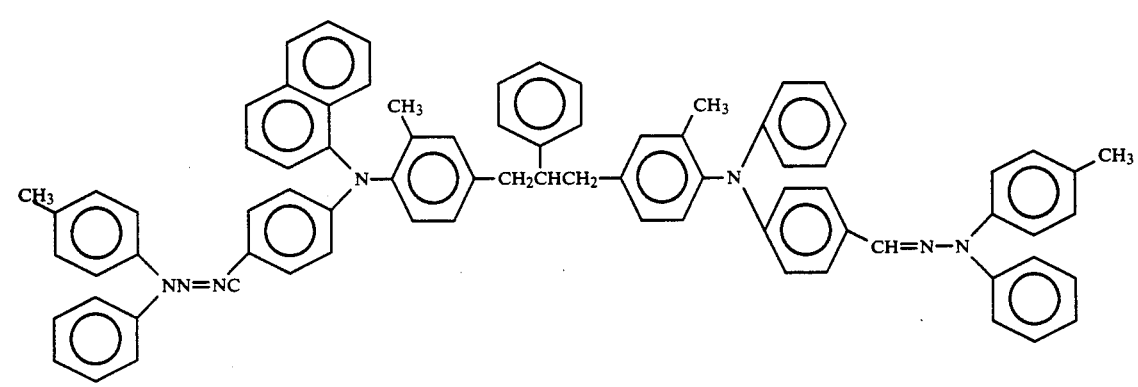
(2-27)

-continued
Exemplary Compounds of arylamine hydrazone compound of the formula (II)

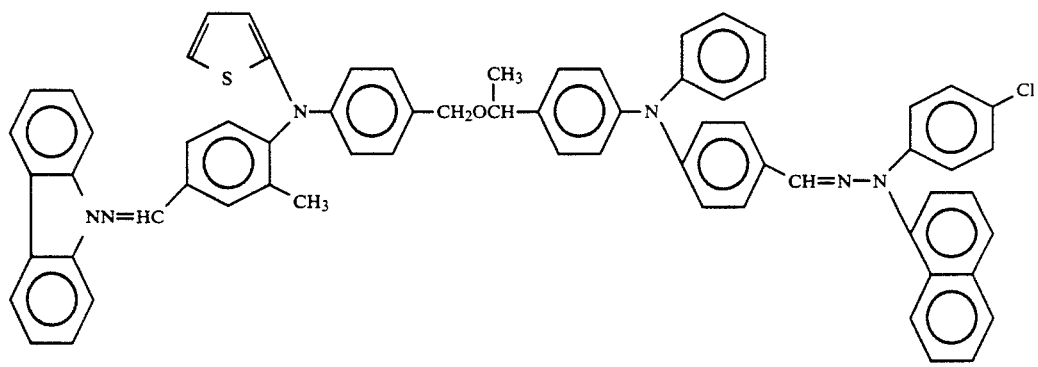
(2-28)

Typical examples of the dihydrazone compound of the formula (III) are given hereinafter. However, the dihydrazone compound useful in the present invention is by no means limited to these typical examples so long as it does not exceed the gist of the present invention.

Exemplary Compounds of dihydrazone compound of the formula (III)

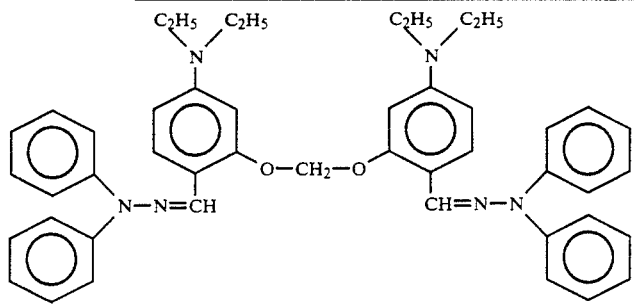
(3-1)

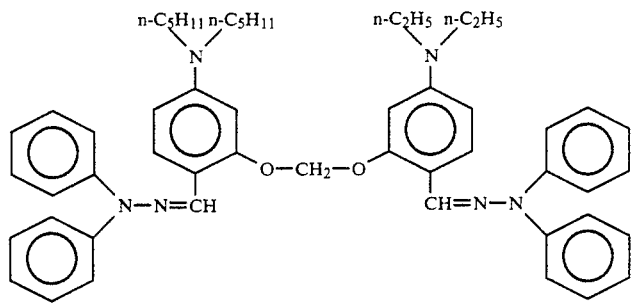
(3-2)

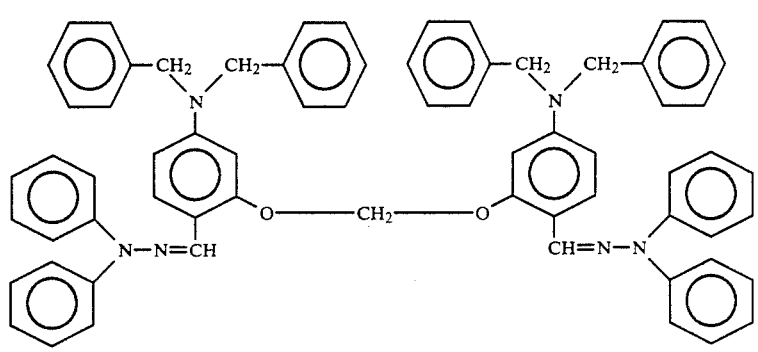
(3-3)

Exemplary Compounds of dihydrazone compound of the formula (III)
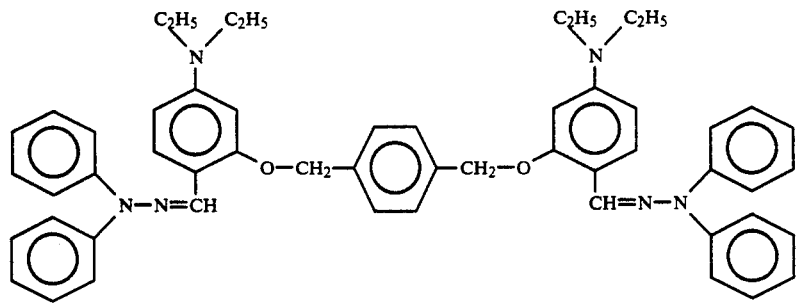
(3-4)
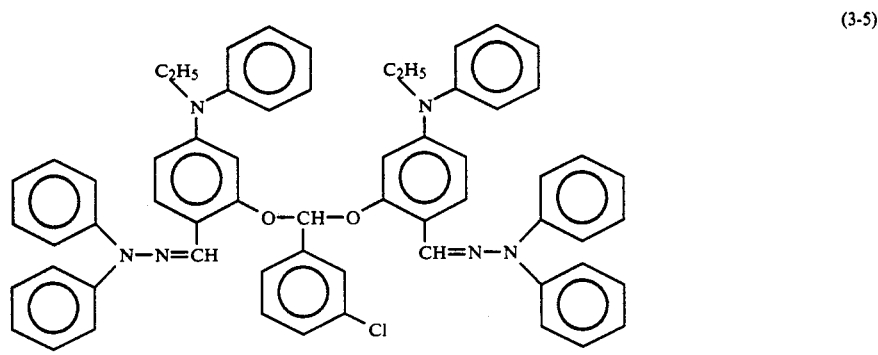
(3-5)
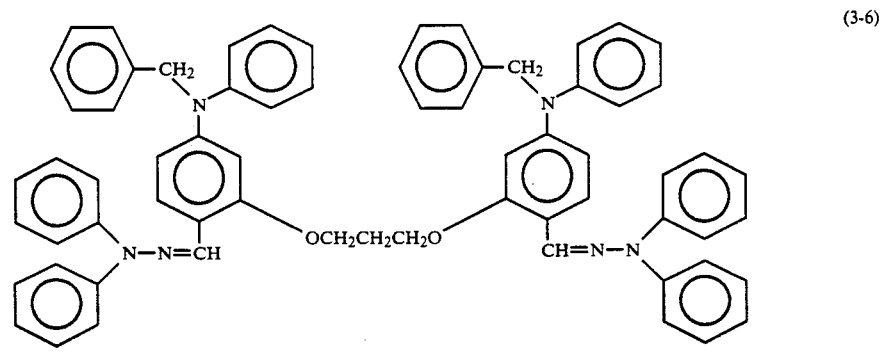
(3-6)
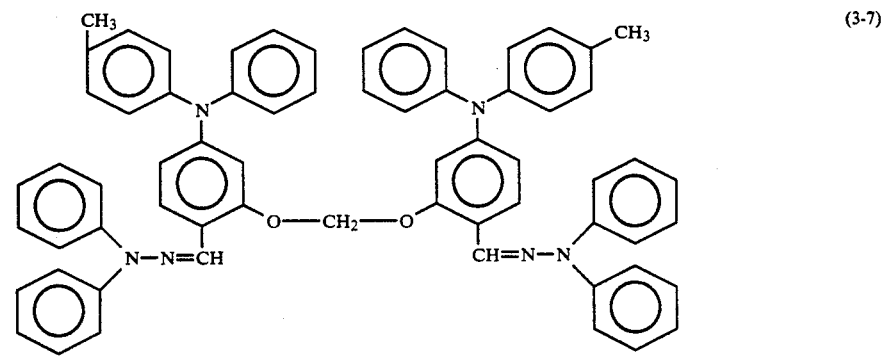
(3-7)

-continued
Exemplary Compounds of dihydrazone compound of the formula (III)
(3-8)
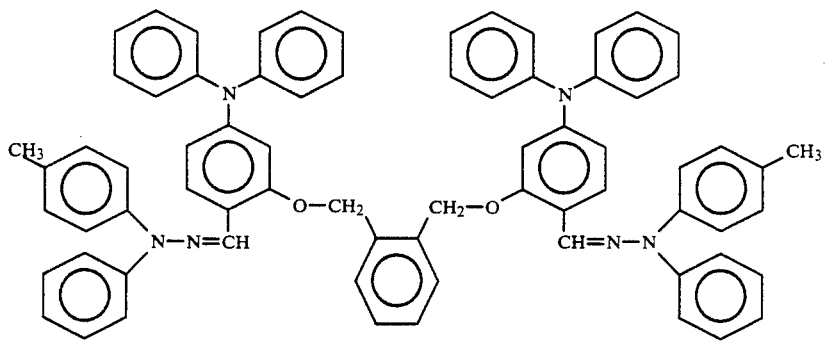
(3-9)
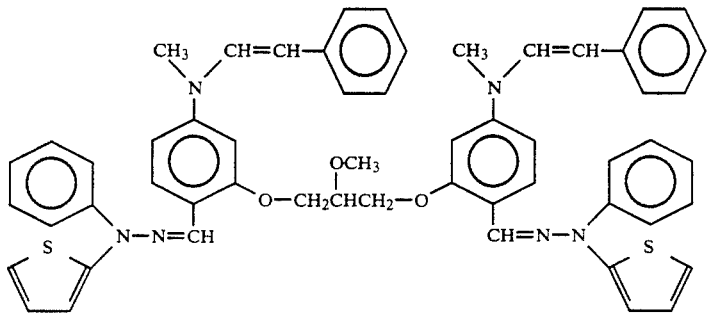
(3-10)
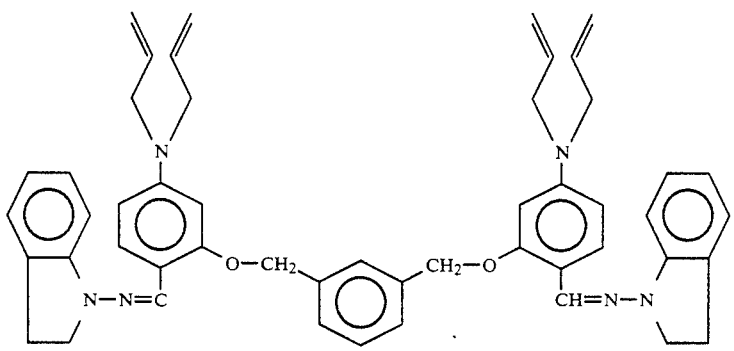
(3-11)
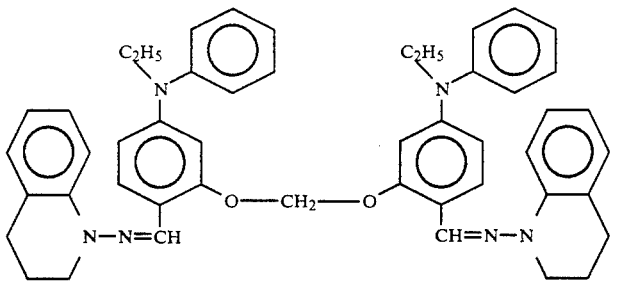
(3-12)
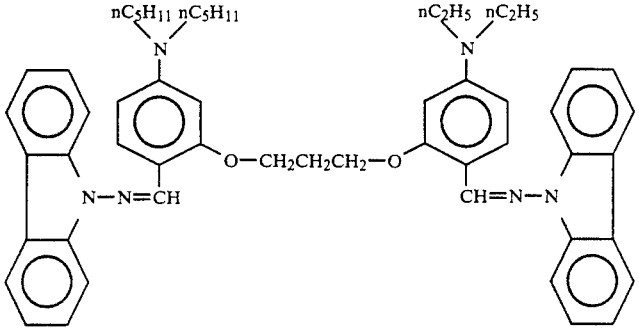

-continued
Exemplary Compounds of dihydrazone compound of the formula (III)
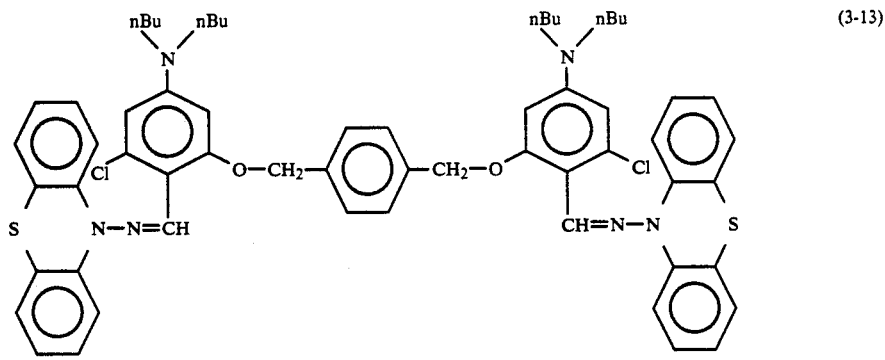
(3-13)
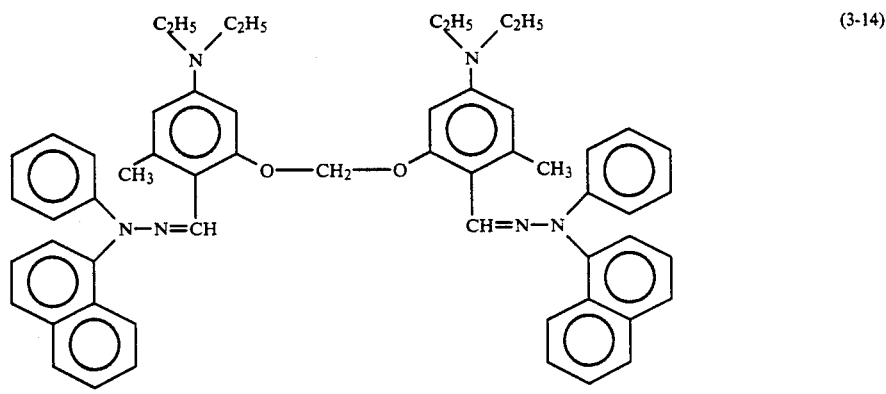
(3-14)
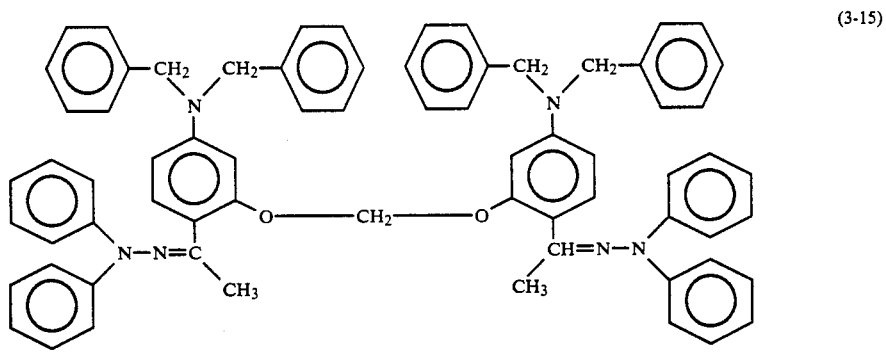
(3-15)
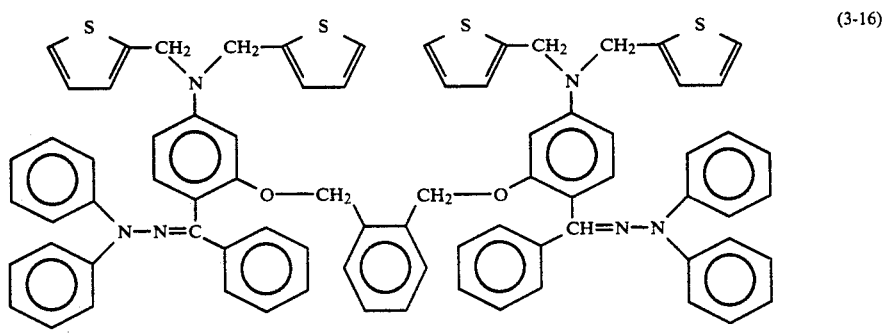
(3-16)

-continued
Exemplary Compounds of dihydrazone compound of the formula (III)

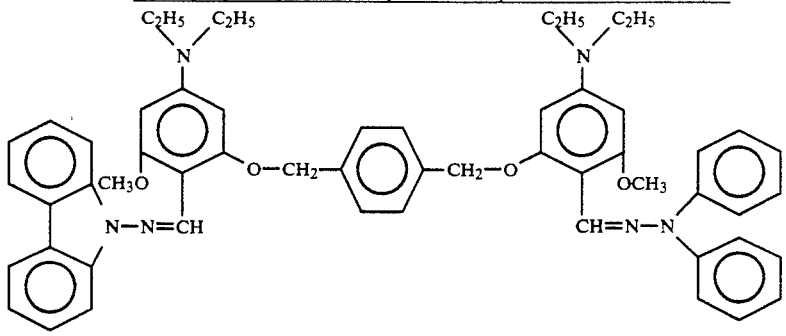
(3-17)

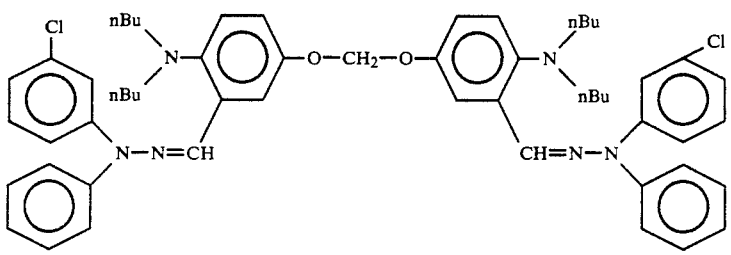
(3-18)

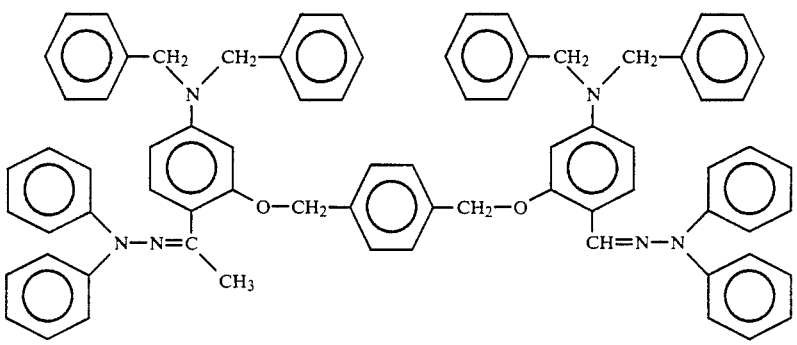
(3-19)

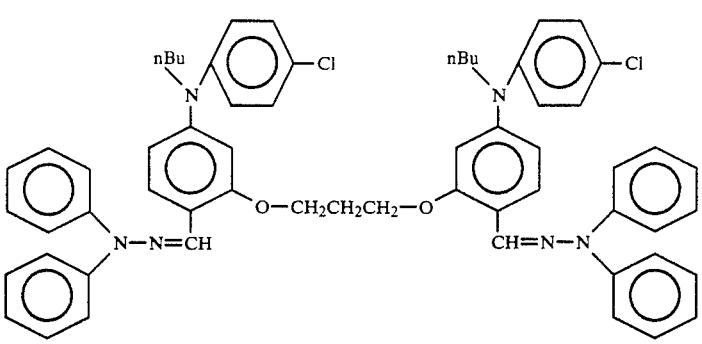
(3-20)

The arylamine hydrazone compound of the formula (I) can be produced by a known method.

For example, a method may be mentioned wherein an arylamine compound as a starting material is subjected to a known formylation or acylation reaction and then dehydration with a desired hydrazine to obtain a desired compound.

(A-1)

In a case where each $R^6$ and $R^8$ in the formula (I) is a hydrogen atom, an arylamine compound of the formula (XII) is reacted with a formylating agent such as N,N-dimethylformamide or N-methylformanilide as shown below:

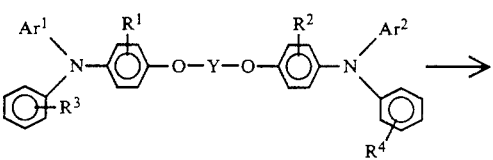
(XII)

-continued (XIII)

(in the formulas (XII) and (XIII), $R^1$, $R^2$, $R^3$, $R^4$, $Ar^1$, $Ar^2$ and Y are as defined with respect to the formula (I), and in the formula (XIII), Z is a hydrogen atom or —CHO) in the presence of phosphorous oxychloride to obtain an aldehyde of the formula (XIII). (Vilsmeyer reaction)

It is possible to use a large excess amount of the formylating agent as a reaction solvent. It is also possible to use a solvent which is inert to the reaction, such as o-dichlorobenzene or benzene.

(A-2)

The compound of the formula (XIII) thus obtained is then subjected to dehydration condensation with a hydrazine of the formula (XIVa) or (XIVb) to produce an arylamine hydrazine of the formula (I).

$R^7$ and $R^5$ of the formula (XIVa) or $R^9$ and $R^{10}$ of the formula (XIVb) may form a heterocyclic ring containing a nitrogen atom, of the formula (VI), (VII), (VIII) or (IX).

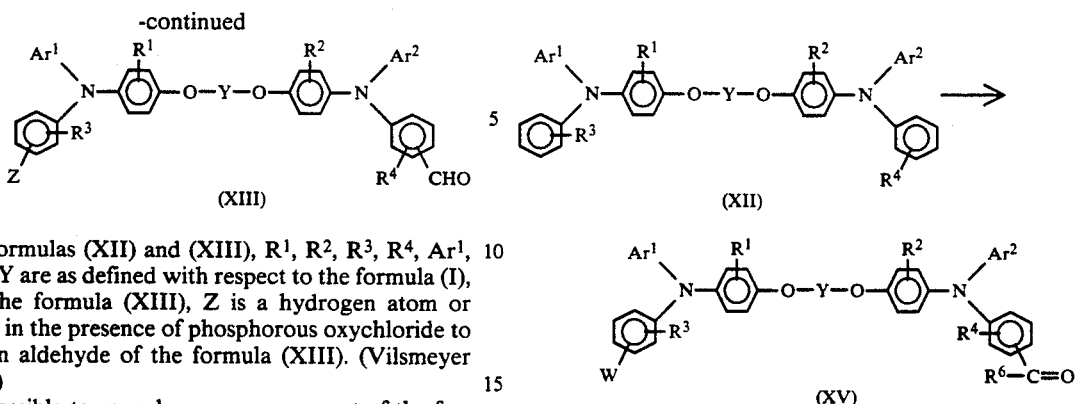

($R^1$, $R^2$, $R^3$, $R^4$, $Ar^1$, $Ar^2$ and Y in the formula (XV) are as defined with respect to the formula (I), and in the formula (XV), W is a hydrogen atom or —C($R^8$)=O, and $R^6$ and $R^8$ which may be the same or different, are as defined with respect to the formula (I)) in the presence of a Lewis acid such as aluminium chloride, iron chloride or zinc chloride, in a solvent such as nitrobenzene, dichloromethane or carbon tetrachloride to obtain a ketone of the formula (XV).

$R^6$ and $R^8$ may be the same or different. When $R^6$ and $R^8$ are not the same, the reaction may be conducted by mixing or stepwise adding the acid chloride to be added.

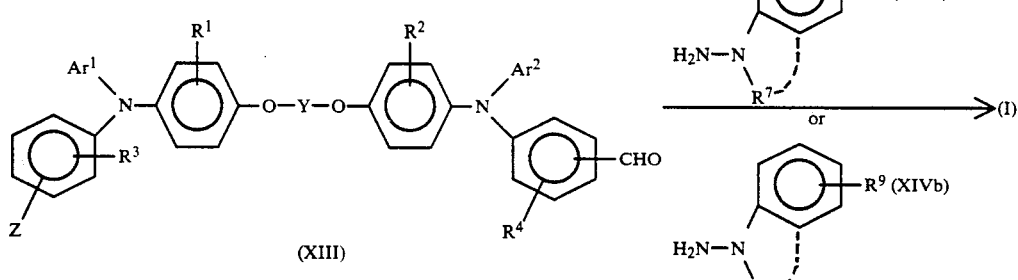

The dehydration condensation may be conducted, if necessary, under heating at 50° C. to 150° C., in a solvent inert to the reaction, such as methanol, ethanol, tetrahydrofuran, cellosolve, N,N-dimethylformamide, benzene or toluene. As occasion demands, an aid such as paratoluene sulfonic acid, hydrochloric acid or sodium acetate may be employed as a reaction accelerator.

Condensation reaction

The compounds of the formulas (XIVa) and (XIVb) may be used singly or as a mixture thereof, or may be reacted stepwise as the case may be.

(B-1)

In a case where each of $R^6$ and $R^8$ in the formula (I) is not a hydrogen atom, an arylamine compound of the formula (XII) is reacted with an acid chloride of the formula: Cl—CO—$R^6$ or Cl—CO—$R^8$, as shown below:

(B-2)

This method can be accomplished by the same reaction as (A-2).

In these reactions, if necessary, it is possible to obtain highly purified products by a known purification such as recrystallization, sublimation or column chromatography after completion of each step or after completion of all steps.

The arylamine hydrazone compound of the formula (II) can be produced by a known method.

For example, a method may be mentioned wherein an arylamine compound as a starting material is subjected to a known formylation or acylation reaction and then subjected to dehydration with a desired hydrazine to obtain a desired compound.

(A-3)

In a case where each of $R^6$ and $R^8$ in the formula (II) is a hydrogen atom, an arylamine compound of the formula (XVI) is reacted with a formylating agent such as N,N-dimethylformamide or N-methylformanilide as shown below:

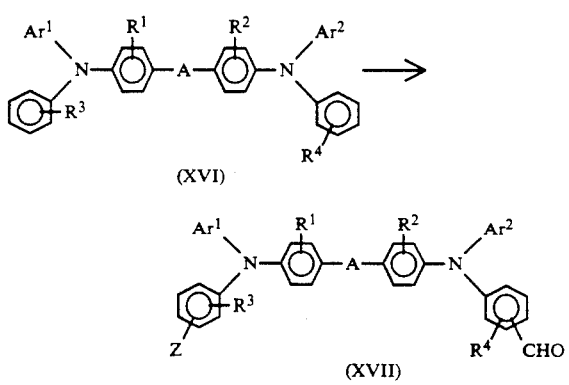

(XVI)

(XVII)

($R^1$, $R^2$, $R^3$, $R^4$, $Ar^1$, $Ar^2$ and A in the formulas (XVI) and (XVII) are as defined with respect to the formula (II) and Z in the formula (XVII) is a hydrogen atom or —CHO) in the presence of phosphorous oxychloride to obtain an aldehyde of the formula (XVII)). (Vilsmeyer reaction)

It is possible to use a large excess amount of the formylating agent as a reaction solvent. It is also possible to use a solvent which is inert to the reaction, such as o-dichlorobenzene or benzene.

(A-4)

Then, the compound of the formula (XVII) thus obtained is dehydratively condensated with a hydrazine of the formula (XVIIIa) or (XVIIIb) as shown below to produce an arylamine hydrazine of the formula (II).

Here, $R^7$ and $R^5$ of the formula (XVIIIa) or $R^9$ and $R^{10}$ of the formula (XVIIIb) may form a heterocyclic ring of the formula (VI), (VII), (VIII) or (IX), which contains a nitrogen atom.

(B-3)

In the case where each of $R^6$ and $R^8$ of the formula (I) is not a hydrogen atom, the arylamine compound of the formula (XVI) is reacted with an acid chloride of the formula: Cl—CO—$R^6$ or Cl—CO—$R^8$, as shown below:

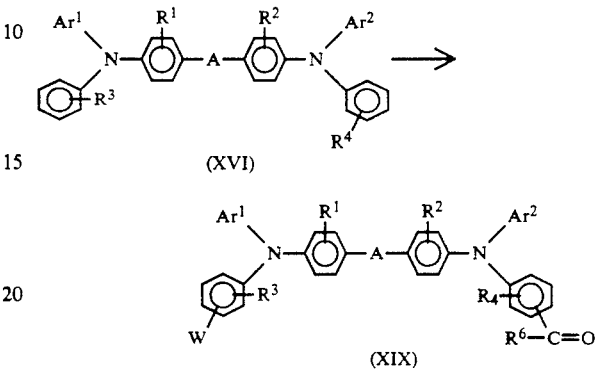

(XVI)

(XIX)

(in the formula (XIX), $R^1$, $R^2$, $R^3$, $R^4$, $Ar^1$, $Ar^2$ and A are as defined with respect to the formula (II), W is a hydrogen atom or —C($R^8$)=O, and $R^6$ and $R^8$ which may be the same or different, are as defined with respect to the formula (II)) in a solvent such as nitrobenzene, dichloromethane or carbon tetrachloride, in the presence of a Lewis acid such as aluminium chloride, iron chloride or zinc chloride to obtain a ketone of the formula (XIX).

$R^6$ and $R^8$ may be the same or different. In the case where $R^6$ and $R^8$ are different, the reaction may be conducted by mixing the acid chloride to be added or adding it stepwise.

(B-4)

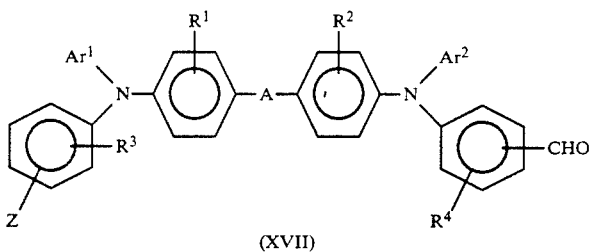

(XVII)

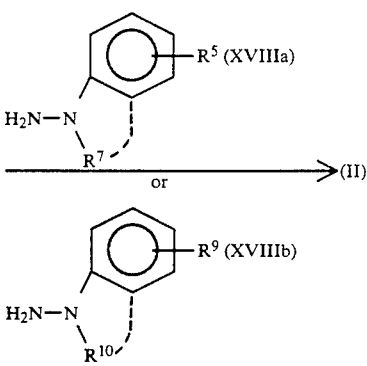

The dehydration-condensation may, if necessary, be conducted in a solvent inert to the reaction, such as methanol, ethanol, tetrahydrofuran, cellosolve, N,N-dimethylformamide, benzene or toluene, under heating at from 50° C. to 150° C. As occasion demands, an aid such as paratoluene sulfonic acid, hydrochloric acid or sodium acetate may be used as a reaction accelerator.

Condensation reaction

The compounds of the formulas (XVIIIa) and (XVIIIb) may be employed singly or as a mixture, or may be reacted stepwise as the case may be.

This method can be accomplished by the same reaction as (A-4).

In these reactions, if necessary, it is possible to obtain highly purified products by a known purification method such as recrystallization, sublimation or column chromatography after completion of each step or after completion of all steps.

The dihydrazone compound of the formula (III) can be produced by a known method.

For example, a method may be mentioned, wherein a diamine compound as a starting material is subjected to a known carbonyl-introduction reaction and then to dehydration with a desired hydrazine to obtain a desired compound.

(A-5)

In the case where each of $R^7$ and $R^8$ of the formula (III) is a hydrogen atom, a diamine compound of the formula (XX) is reacted with a formylating agent such as N,N-dimethylformamide or N-methylformanilide as shown below:

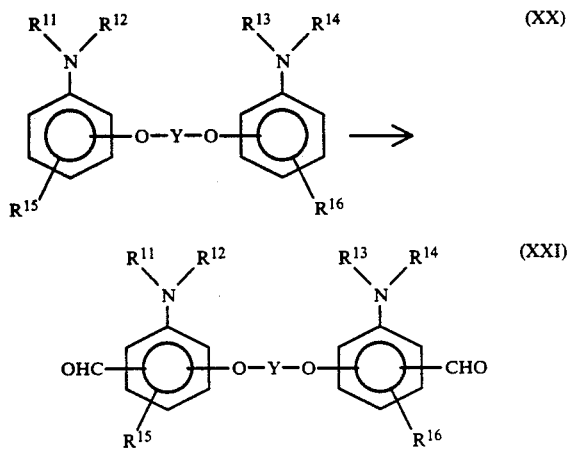

($Y$, $R^{11}$, $R^{12}$, $R^{13}$, $R^{14}$, $R^{15}$ and $R^{16}$ of the formulas (XX) and (XXI) are as defined with respect to the formula (III)) in the presence of phosphorous oxychloride to obtain a dialdehyde of the formula (XXI). (Vilsmeyer reaction)

It is possible to employ a large excess amount of the formylating agent as a reaction solvent. It is also possible to employ a solvent inert to the reaction, such as o-dichlorobenzene or benzene.

(A-6)

Then, the compound of the formula (XXI) thus obtained is dehydratively condensated with a hydrazine of the formula: $H_2N-Q^3$ or $H_2N-Q^4$, where $Q^3$ and $Q^4$ are as defined with respect to the formula (III), to produce a dihydrazone of the formula (III) as shown below:

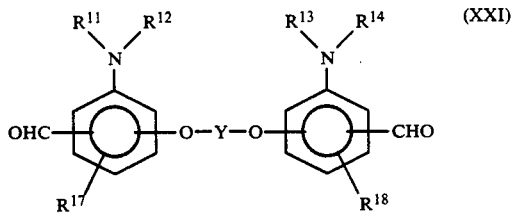

The dehydratively condensation may be, if necessary, conducted under heating at from 50° C. to 150° C., in a solvent inert to the reaction, such as methanol, ethanol, tetrahydrofuran, cellosolve, N,N-dimethylformamide, benzene or toluene. As occasion demands, an aid such as paratoluene sulfonic acid, hydrochloric acid or sodium acetate may be employed as a reaction accelerator.

Hydrazonization $Q^3$ and $Q^4$ may be the same or different. In the case where $Q^3$ and $Q^4$ are different, the reaction may be conducted by mixing a hydrazine to be added or adding it stepwise.

(B-5)

In the case where each of $R^7$ and $R^8$ in the formula (III) is not a hydrogen atom, a diamine compound of the formula (XX) is reacted with an acid chloride of the formula: $Cl-CO-R^{17}$ or $Cl-CO-R^{18}$, as shown below:

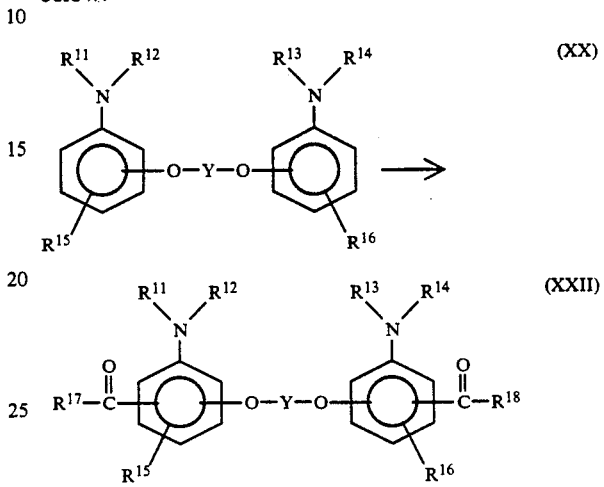

($Y$, $R^{11}$, $R^{12}$, $R^{13}$, $R^{14}$, $R^{15}$, $R^{16}$, $R^{17}$ and $R^{18}$ in the formulas (XXI) and (XXII) are as defined with respect to the formula (III)) in the presence of a Lewis acid such as aluminium chloride, iron chloride or zinc chloride in a solvent such as nitrobenzene, dichloromethane or carbon tetrachloride to obtain a diketone of the formula (XXII).

$R^{17}$ and $R^{18}$ may be the same or different. In the case where $R^{17}$ and $R^{18}$ are different, the reaction may be conducted by mixing the acid chloride to be added or adding it stepwise.

(B-6)

This reaction can be conducted by the same reaction as (A-6).

It is possible to obtain highly purified products by a known purification method such as recrystallization, sublimation or column chromatography, after completion of each step or after completion of all steps.

The electrophotographic photoreceptor of the present invention has a photosensitive layer containing at least one member selected from the group consisting of the hydrazone compounds of the formulas (I), (II) and (III).

The hydrazone compound of the formula (I), (II) or (III) exhibits excellent properties as an organic photoconductive material. Especially when used as a carrier transport material, it gives a photoreceptor having high sensitivity and excellent durability.

Various types are known for the photosensitive layer for an electrophotographic photoreceptor. The photosensitive layer of the electrophotographic photoreceptor of the present invention may be any one of such types. For example, the following types may be mentioned:

(i) a photosensitive layer having the hydrazone compound and, as occasion demands, a pigment useful as a sensitizing agent and a carrier attracting compound added in a binder.

(ii) a photosensitive layer having photoconductive particles capable of generating an electric charge carrier at an extremely high efficiency upon absorption of light and the hydrazone compound added in a binder.

(iii) a photosensitive layer having laminated a carrier transport layer composed of the hydrazone compound and a binder and a carrier generation layer composed of photoconductive particles capable of generating an electric charge carrier at an extremely high efficiency upon absorption of light, or composed of such photoconductive particles and a binder.

In such a photosensitive layer, a known other hydrazone compound or stilbene compound having excellent properties as an organic photoconductive material, may be incorporated together with at least one member selected from the group consisting of the hydrazone compounds of the formulas (I), (II) and (III).

In the present invention, when at least one member selected from the group consisting of the hydrazone compounds of the formulas (I), (II) and (III) is used in a carrier transport layer of a photosensitive layer which comprises two layers of the carrier transport layer and a carrier generation layer, it is possible to obtain a photoreceptor having particularly high sensitivity and low residual potential and which has excellent durability such that even when used repeatedly, the change in the surface potential, the deterioration of the sensitivity or the accumulation of the residual potential is small.

The electrophotographic photoreceptor of the present invention can be prepared in accordance with a usual method by dissolving at least one member selected from the group consisting of the hydrazone compounds of the formulas (I), (II) and (III) together with the binder in a suitable solvent, adding photoconductive particles capable of generating an electric charge carrier at an extremely high efficiency upon absorption of light, a sensitizing dye, an electron attracting compound, a plasticizer, a pigment or other additives, as the case requires, to obtain a coating solution, and then applying such a coating solution on an electrically conductive support, followed by drying to form a photosensitive layer having a thickness of from a few μm to a few tens μm. The photosensitive layer comprising two layers of the carrier generation layer and the carrier transport layer can be prepared either by applying the above mentioned coating solution on the carrier generation layer, or forming a carrier generation layer on the carrier transport layer obtained by coating the above mentioned coating solution The solvent useful for the preparation of the coating solution is a solvent capable of dissolving the hydrazone compound, for example, an ether such as tetrahydrofuran or 1,4-dioxane; a ketone such as methyl ethyl ketone or cyclohexanone; an aromatic hydrocarbon such as toluene or xylene; an aprotic polar solvent such as N,N-dimethylformamide, acetonitrile, N-methyl pyrrolidone or dimethyl sulfoxide; an ester such as ethyl acetate, methyl formate or methyl cellosolve acetate; or a chlorinated hydrocarbon such as dichloroethane or chloroform. It is of course necessary to select among them the one capable of dissolving the binder. The binder may be a polymer or copolymer of a vinyl compound such as styrene, vinyl acetate, vinyl chloride, an acrylate, a methacrylate or butadiene, or various polymers compatible with a styrene compound, such as polyvinyl acetal, polycarbonate, polyester, polysulfone, polyphenyleneoxide, polyurethane, cellulose ester, cellulose ether, a phenoxy resin, a silicone resin and an epoxy resin. The binder is used usually in an amount within a range of from 0.5 to 30 times by weight, preferably from 0.7 to 10 times by weight, relative to the hydrazone compound.

The photoconductive particles, dyes, pigments or electron attracting compounds to be added to the photosensitive layer may be those well known in the art. The photoconductive particles capable of generating electron charge carriers at an extremely high efficiency upon absorption of light, include inorganic photoconductive particles such as selenium, selenium-tellurium alloy, selenium-arsenic alloy and a cadmium sulfide and amorphous silicon; and organic photoconductive particles such as metal-containing phthalocyanine, perinone dyes, thioindigo dyes, quinacridone, perylene dyes, anthraquinone dyes, azo dyes, bisazo dyes, trisazo dyes, tetrakisazo dyes and cyanine dyes. (Particularly, a photoreceptor having an improved sensitivity against laser beam, can be obtained by combining with the metal-containing phthalocyanine.) The dyes include, for example, triphenylmethane dyes such as Methyl Violet, Brilliant Green and Crystal Violet; thiazine dyes such as Methylene Blue; quinone dyes such as quinizarin and cyanine dyes as well as pyrylium salts, thiapyrylium salts and benzopyrylium salts. The electron attracting compound capable of forming a carrier transport complex together with the hydrazone compound, includes, for example, quinones such as chloranil, 2,3-dichloro-1,4-naphthoquinone, 1-nitroanthraquinone, 1-chloro-5-nitroanthraquinone, 2-chloroanthraquinone and phenanthrenequinone; aldehydes such as 4-nitrobenzaldehyde; ketones such as 9-benzoylanthracene, indanedione, 3,5-dinitrobenzophenone, 2,4,7-trinitrofluorenone, 2,4,5,7-tetranitrofluorenone and 3,3',5,5'-tetranitrobenzophenone; acid anhydrides such as phthalic anhydride and 4-chloronaphthalic anhydride; cyano compounds such as tetracyanoethylene, terephthalal malononitrile, 9-anthrylmethylidene malononitrile, 4-nitrobenzal malononitrile and 4-(p-nitrobenzoyloxy)benzal malononitrile; and phthalides such as 3-benzalphthalide, 3-(α-cyano-p-nitrobenzal)phthalide and 3-(α-cyano-p-nitrobenzal)-4,5,6,7-tetrachlorophthalide.

Further, the photosensitive layer of the electorphographic photoreceptor according to this invention may contain a well-known plasticizer for the improvement of the film-forming properties, flexibility and mechanical strength. The plasticizer to be added to the above coating solution for this purpose may be a phthalic ester, a phosphoric ester, an epoxy compound, a chlorinated paraffin, a chlorinated fatty acid ester or an aromatic compound such as methylnaphthalene. In a case where the hydrazone compound is used as a carrier transport material in the carrier transport layer, the coating solution may be of the above described composition, but photoconductive particles, dyes, pigments, electron attracting compounds and the like may be eliminated or added in a small amount. The carrier generation layer in this case includes a layer prepared by forming the above mentioned photoconductive particles into a film by means of e.g. vapor deposition, and a thin layer prepared by applying a coating solution which is obtained by dissolving or dispersing the photoconductive particles and optionally a binder polymer as well as an organic photoconductive material, a dye and an electron attracting compound in a solvent, and drying it.

The photoreceptor thus formed may further have an adhesive layer, an intermediate layer, a transparent insulation layer or the like, as the case requires. As the electrically conductive support on which the photosensitive layer is formed, any material which is commonly used for electrophotographic photoreceptors, can be employed. Specifically, a drum or sheet of a metal such as aluminum, stainless steel or copper, or a laminate of foils of such metals, or a vapor-deposition product of such metals, may be mentioned. Further, a plastic film, a plastic drum, paper or a paper tube electrified by coating a conductive material such as metal powder, carbon black, copper iodide or a polymer electrolyte together with an appropriate binder, may be mentioned. Further, an electrically conductive plastic sheet or drum containing a conductive substance such as metal powder, carbon black or carbon fiber, may be mentioned.

The electrophotographic photoreceptor of the present invention has a very high sensitivity and a small residual potential which is likely to cause fogging, and it has a feature of excellent durability since the accumulation of the residual potential due to repeated use and fluctuations in the surface potential and in the sensitivity are minimum as the light-fatigue is minimum.

Now, the present invention will be described in further detail with reference to Examples. However, it should be understood that the present invention is by no means restricted by such specific Examples. In the Examples, "parts" means "parts by weight".

PREPARATION EXAMPLE 1

1.5 g of bis(p-diphenylaminophenoxy)methane:

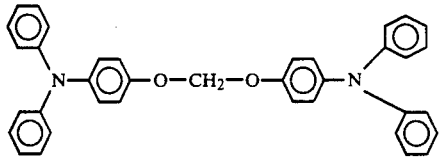

was dissolved in 30 ml of N,N-dimethylformamide, and 0.64 ml of phosphorous oxychloride was added thereto, and then the reaction was conducted at 60° C. for 5 hours. The reaction solution was left to cool, poured in 200 g of ice water, hydrolyzed with sodium hydroxide, and further subjected to filtration and purification treatments by known methods to obtain 0.61 g of a monoformylated product as yellow oily products and 0.33 g of a diformylated product as yellow oily products.

These compounds were found to be compounds of the following formulas, respectively, from the following values of elemental analysis, the mass spectrometric analysis and the infrared absorption spectrum analysis:

(1) Monoformylated compound

| Elemental analysis: As $C_{38}H_{30}N_2O_3$ | | | |
|---|---|---|---|
| | C % | H % | N % |
| Calculated | 81.12 | 5.37 | 4.98 |
| Found | 80.21 | 5.41 | 4.87 |

Results of mass spectrometric analysis:
As $C_{38}H_{30}N_2O_3$

MW = 562
M+ = 562

-continued

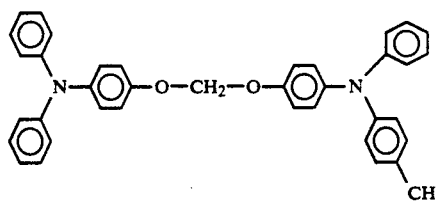

(2) Diformylated compound

| Elemental analysis: As $C_{39}H_{30}N_2O_4$ | | | |
|---|---|---|---|
| | C % | H % | N % |
| Calculated | 79.30 | 5.12 | 4.74 |
| Found | 79.21 | 5.21 | 4.80 |

Results of mass spectrometric analysis:
As $C_{39}H_{30}N_2O_4$

MW = 590
M+ = 590

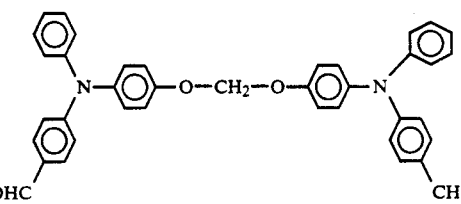

PREPARATION EXAMPLE 2

0.61 g of the monoformyl compound synthesized in Preparation Example 1 and 0.28 g of 1,1-diphenylhydrazine were reacted in the presence of an acetic acid catalyst in a mixed solution of 3 ml of tetrahydrofuran and 5 ml of methanol at 50° to 60° C. for 2 hours. Then, the reaction solution was poured in 500 ml of methanol and subjected to filtration and purification treatments by known methods to obtain 0.79 g of a yellow solid.

This compound was found to be a monohydrazone compound of the following formula (Exemplary Compound No. 1-1 as mentioned above) from the following values of elemental analysis, the mass spectrometric analysis and the infrared absorption spectrum analysis (FIG. 1):

| Elemental analysis: As $C_{50}H_{40}N_4O_2$ | | | |
|---|---|---|---|
| | C % | H % | N % |
| Calculated | 82.39 | 5.53 | 7.69 |
| Found | 83.29 | 5.60 | 7.24 |

Results of mass spectrometric analysis:
As $C_{50}H_{40}N_4O_2$

MW = 728,
M+ = 728

-continued

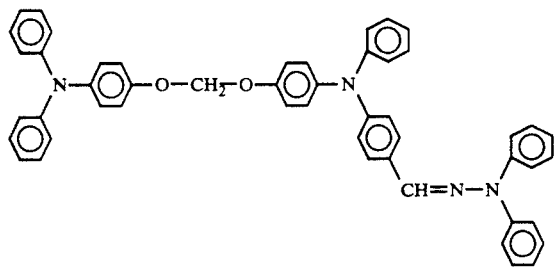

PREPARATION EXAMPLE 3

0.33 g of the diformyl compound synthesized in Preparation Example 1 was reacted with 0.29 g of 1,1-diphenylhydrazine in the presence of an acetic acid catalyst in a mixed solution of 3 ml of tetrahydrofuran and 5 ml of methanol at 50° to 60° C. for 2 hours. Then, the reaction solution was poured in 500 ml of methanol and subjected to filtration and purification treatments by known methods to obtain 0.22 g of a yellow solid.

Figure 2:
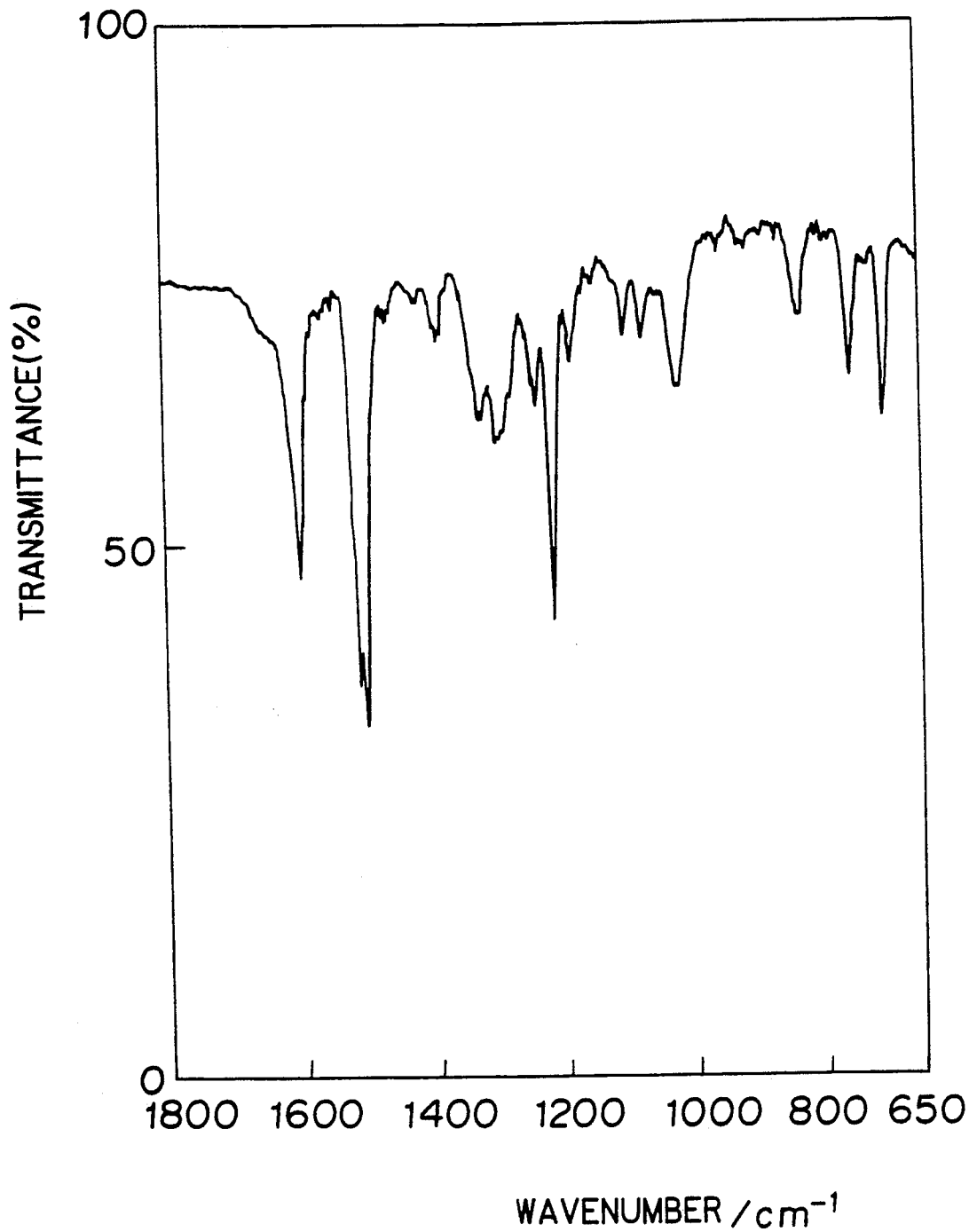
FIG. 2 is an infrared absorption spectrum of the dihydrazone compound obtained in Preparation Example 3.
Figure 3:
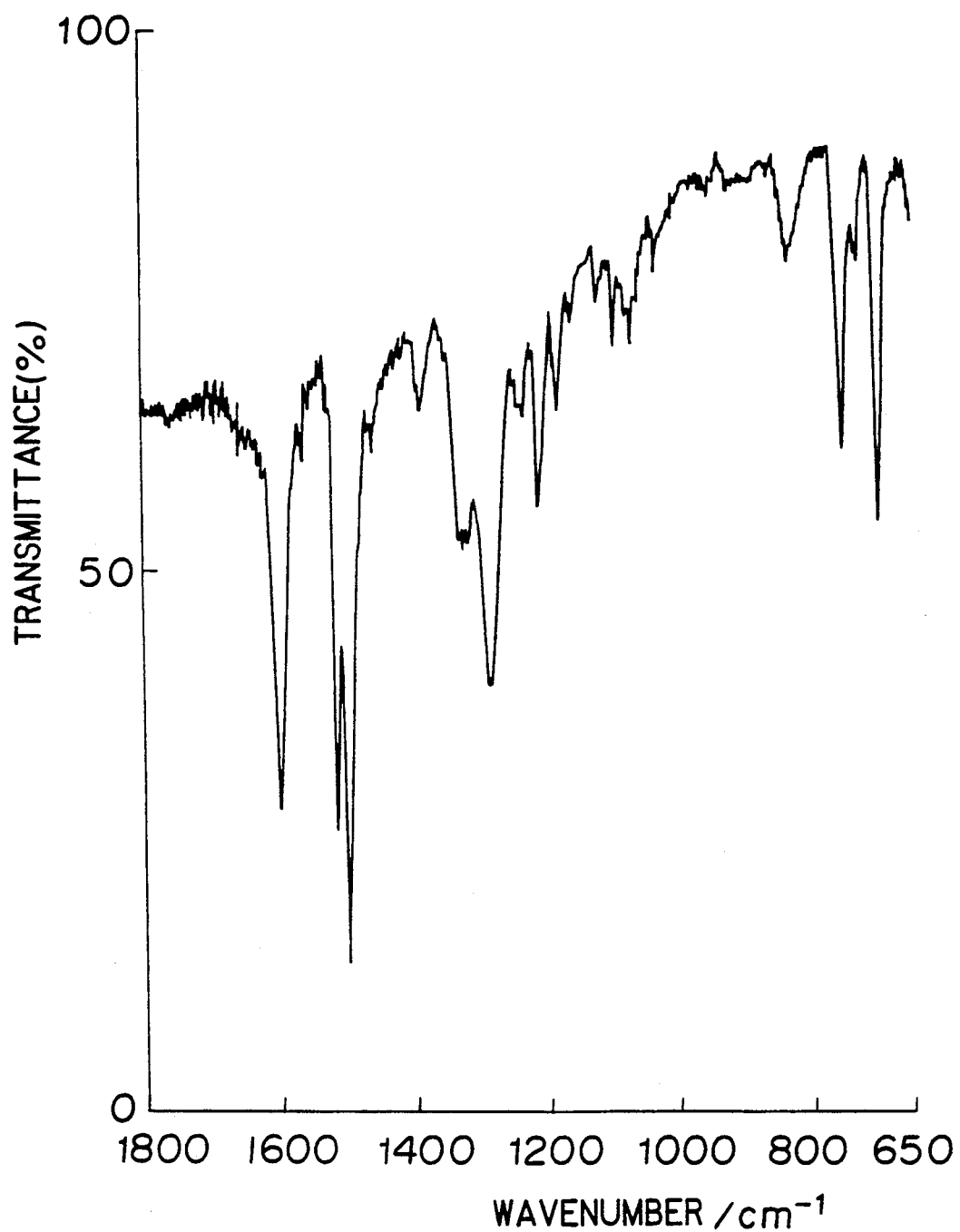
FIG. 3 is an infrared absorption spectrum of the monohydrazone compound obtained in Preparation Example 5.

This compound was found to be a dihydrazone compound of the following formula (Exemplary Compound No. 1-21 as mentioned above) from the following values of elemental analysis and the infrared absorption spectrum analysis (FIG. 2):

This dispersion was coated by a wire bar on an aluminium layer vapor-deposited on a polyester film having a thickness of 100 μm so that the weight after drying would be 0.2 g/m², followed by drying to form a carrier generation layer.

A coating solution prepared by dissolving 70 parts of the hydrazine compound prepared in Preparation Example 3 and 100 parts of a polycarbonate as shown below in 900 parts of dioxane, was coated thereon and dried to form a carrier transport layer having a thickness of 17 μm.

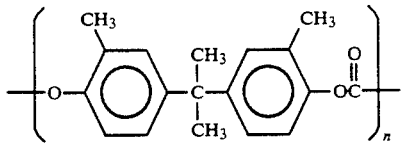

With respect to the electrophotographic photoreceptor having a photosensitive layer comprising two layers thus obtained, the sensitivity i.e. the half-decay exposure intensity was measured and found to be 2.7 $(\mu W/cm^2)^{-1}$.

Here, the half-decay exposure intensity was determined by firstly charging the photoreceptor in a dark place with corona discharge at −4.8 KV, then subjecting to exposure to a light of 775 nm, and measuring the

| | Elemental analysis: As $C_{63}H_{50}N_6O_2$ | | |
|---|---|---|---|
| | C % | H % | N % |
| Calculated | 81.97 | 5.46 | 9.10 |
| Found | 81.83 | 5.55 | 9.17 |

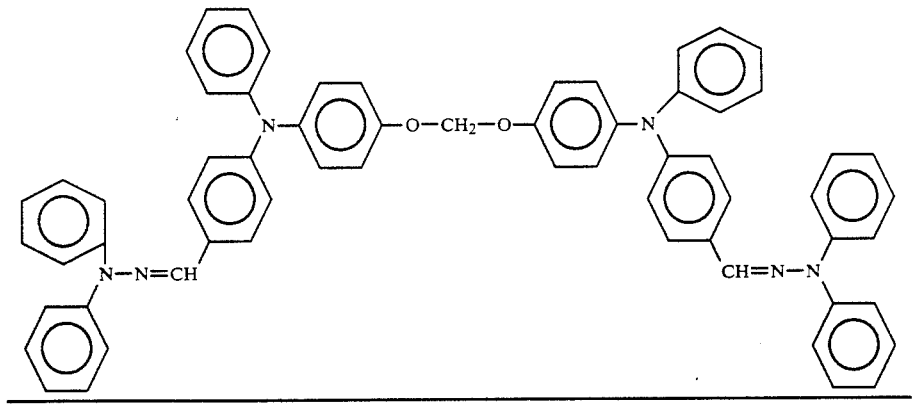

exposure intensity required until the surface potential decayed from 500 V to 250 V.

EXAMPLE 1

1.0 part of a titanium oxyphthalocyanine dye and 0.5 part of polyvinylbutyral (Tradename: Polyvinylbutyral #6000, manufactured by Denki Kagaku Kogyo K. K.) were dispersed and pulverized in 30 parts of 4-methoxy-4-methylpentanone-2 (manufactured by Mitsubishi Kasei Corporation).

EXAMPLE 2

A photoreceptor was produced in the same manner as in Example 1 except that an unsymmetrical disazo dye of the following formula was used instead of the phthalocyanine dye used in Example 1, then subjected to exposure to incandescent light, and measuring the half-decay exposure intensity to find to be 1.0 lux.sec.

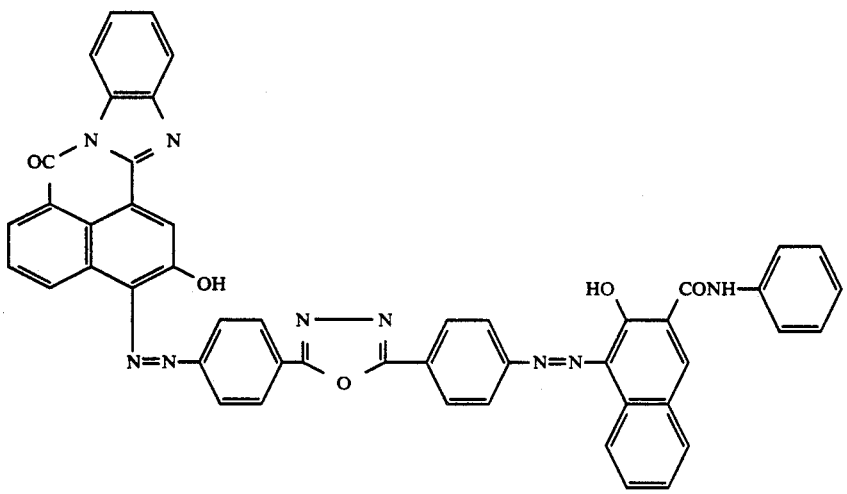

EXAMPLES 3 TO 17

Electrophotographic photoreceptors were produced in the same manner as in Example 1 except that hydrazone compounds as shown in Table 1, synthesized in the same manner as in Preparation Example 2 or 3, and the titanium oxyphthalocyanine dye used in Example 1 was used for the carrier generation layer, and their sensitivities are shown in the following Table 1.

TABLE 1

| Example | Exemplary Compound No. | Sensitivity $(\mu W/cm^2)^{-1}$ |
|---|---|---|
| 3 | 1-1 | 2.4 |
| 4 | 1-2 | 1.8 |
| 5 | 1-5 | 2.3 |
| 6 | 1-8 | 1.9 |
| 7 | 1-11 | 2.4 |
| 8 | 1-12 | 2.2 |
| 9 | 1-18 | 1.8 |
| 10 | 1-22 | 1.8 |
| 11 | 1-25 | 2.3 |
| 12 | 1-26 | 2.0 |
| 13 | 1-28 | 1.7 |
| 14 | 1-29 | 2.2 |
| 15 | 1-33 | 2.1 |
| 16 | 1-37 | 2.2 |
| 17 | 1-40 | 1.9 |

PREPARATION EXAMPLE 4

5.2 g of bis(p-diphenylamino)-1,3-diphenylpropane:

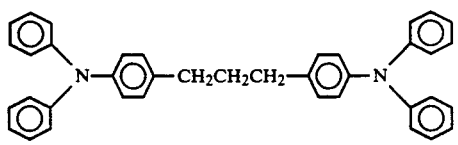

was dissolved in 52 ml of N,N-dimethylformamide, and 1.9 ml of phosphorous oxychloride was added thereto, and then the reaction was conducted at 60° C. for 1 hour and 30 minutes.

The reaction solution was left to cool and then poured in 200 g of ice water, hydrolyzed with sodium hydroxide, and then subjected to filtration and purification treatments by known methods to obtain 2.2 g of a monoformyl compound as a yellow oil and 2.9 g of a bisformyl compound as a yellow oil.

These compounds were found to be compounds of the following formulas, respectibly, from the following values of elemental analysis, the mass spectrometric analysis and the infrared absorption spectrum analysis:

(1) Monoformyl compound

| Elemental analysis: As $C_{40}H_{34}ON_2$ | | | |
|---|---|---|---|
| | C % | H % | N % |
| Calculated | 85.99 | 6.13 | 5.01 |
| Found | 85.90 | 6.24 | 4.95 |

| Results of mass spectrometric analysis: As $C_{40}H_{34}ON_2$ |
|---|
| MW = 558 |
| M+ = 558 |

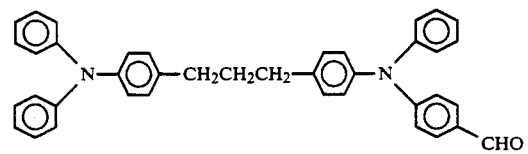

(2) Diformyl compound

| Elemental analysis: As $C_{41}H_{34}O_2N_2$ | | | |
|---|---|---|---|
| | C % | H % | N % |
| Calculated | 83.93 | 5.84 | 4.77 |
| Found | 83.69 | 6.01 | 4.71 |

| Results of mass spectrometric analysis: As $C_{41}H_{34}O_2N_2$ |
|---|
| MW = 586 |
| M+ = 586 |

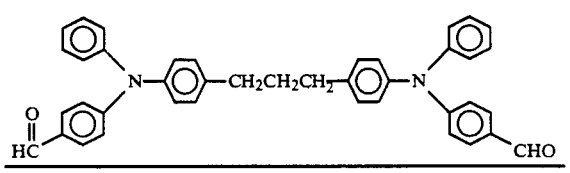

PREPARATION EXAMPLE 5

2.2 g of monoformyl compound synthesized in Preparation Example 4 and 1.5 g of 1,1-diphenylhydrazine were reacted in the presence of an acetic acid catalyst in a mixed solution of 13 ml of tetrahydrofuran and 6 ml of methanol at room temperature for 12 hours.

Then, the reaction solution was poured in 500 ml of methanol and subjected to filtration and purification treatments by known methods to obtain 1.7 g of yellow crystals (melting point: 67°-68° C.).

This compound was found to be a monohydrazone compound of the following formula (Exemplary Compound No. 2-1 as mentioned above) from the following values of elemental analysis, the mass spectrometric analysis and the infrared absorption spectrum analysis:

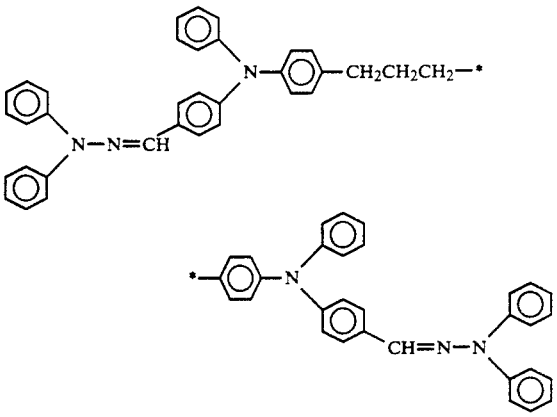

|  | Elemental analysis: As $C_{52}H_{44}N_4$ | | |
|---|---|---|---|
|  | C % | H % | N % |
| Calculated | 86.15 | 6.12 | 7.73 |
| Found | 86.01 | 6.35 | 7.61 |

| Results of mass spectrometric analysis: As $C_{52}H_{44}N_4$ |
|---|
| MW = 724 |
| $M^+$ = 724 |

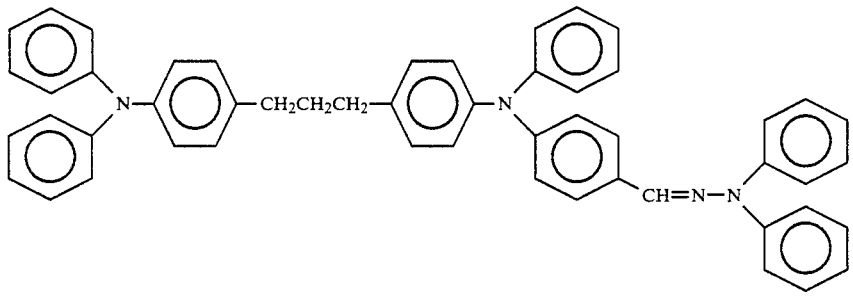

PREPARATION EXAMPLE 6

2.9 g of the diformyl compound synthesized in Preparation Example 4 was reacted with 3.6 g of 1,1-diphenylhydrazine in the presence of an acetic acid catalyst in a mixed solution of 17 ml of tetrahydrofuran and 16 ml of methanol at room temperature for 12 hours.

Then, the reaction solution was poured in 500 ml of methanol and further subjected to filtration and purification treatments by known methods to obtain 3.6 g of yellow crystals (melting point: 205°-205.5° C.).

Figure 4:
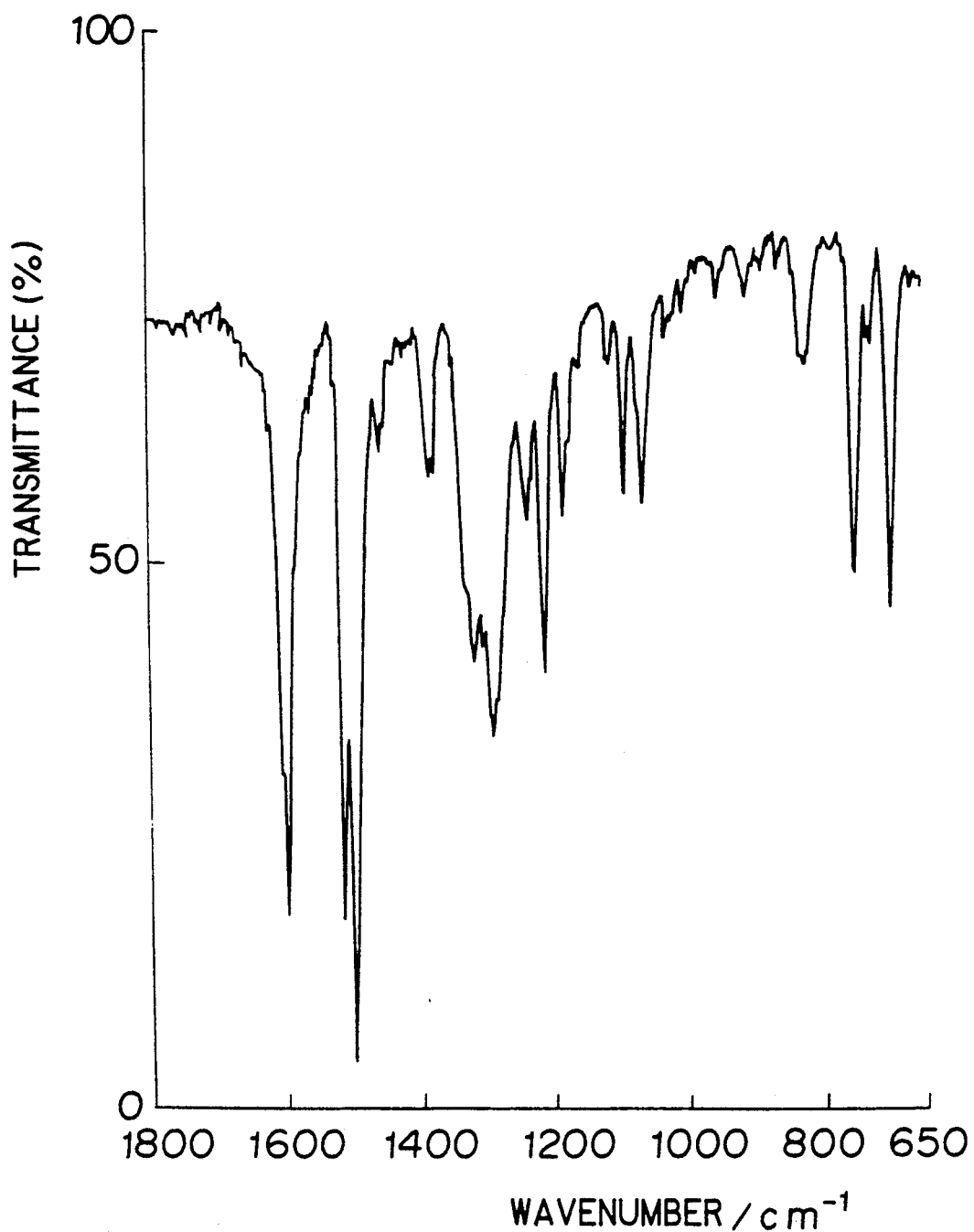
FIG. 4 is an infrared absorption spectrum of the dihydrazone compound obtained in Preparation Example 6.

This compound was found to be a dihydrazone compound of the following formula (Exemplary Compound No. 2-14 as mentioned above) from the following values of elemental analysis and the infrared absorption spectrum analysis (FIG. 4):

|  | Elemental analysis: As $C_{65}H_{54}N_6$ | | |
|---|---|---|---|
|  | C % | H % | N % |
| Calculated | 84.94 | 5.92 | 9.14 |
| Found | 85.04 | 5.90 | 9.03 |

EXAMPLE 18

1.0 part of titanium oxyphthalocyanine dye and 0.5 part of polyvinylbutyral (tradename: Polyvinylbutyral #6000, manufactured by Denki Kagaku Kogyo K. K.) were dispersed and pulverized in 30 parts of 4-methoxy-4-methylpentanone-2 (manufactured by Mitsubishi Kasei Corporation).

This dispersion was coated by a wire bar on an aluminium layer vapor-deposited on a polyester film having a thickness of 100 μm so that the weight after drying would be 0.2 g/m², followed by drying to form a carrier generation layer.

A coating solution prepared by dissolving 70 parts of the hydrazone compound prepared in Preparation Example 6 and 100 parts of a polycarbonate as shown below in 900 parts of dioxane, was coated thereon and dried to form a carrier transport layer having a thickness of 17 μm.

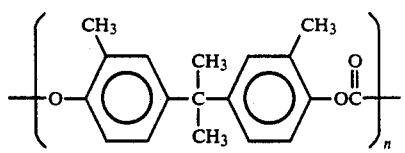

With respect to the electrophotographic photoreceptor having a photosensitive layer comprising two layers thus obtained, the sensitivity i.e. the half-decay exposure intensity was measured and found to be 2.8 $(\mu W/cm^2)^{-1}$.

Here, the half-decay exposure intensity was determined by firstly charging the photoreceptor in a dark place with corona discharge at $-4.8$ KV, then subjecting it to exposure to a light of 775 nm, and measuring the exposure intensity required until the surface potential decayed from 500 V to 250 V.

EXAMPLE 19

A photoreceptor was produced in the same manner as in Example 1 except that an unsymmetrical disazo dye of the following formula was used instead of the phthalocyanine dye used in Example 1. This photoreceptor was subjected to exposure to incandescent light, and the half-decay exposure intensity was measured and found to be 1.0 lux.sec.

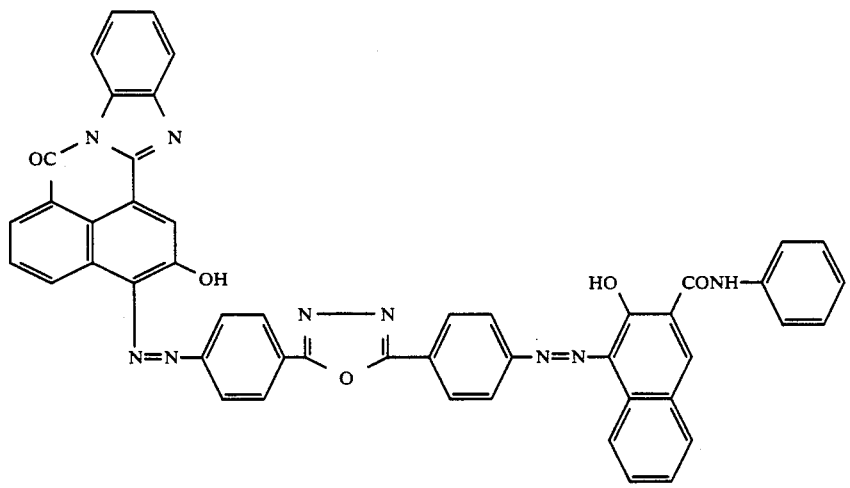

EXAMPLES 20 TO 25

Electrophotographic photoreceptors were produced in the same manner as in Example 18 except that hydrazone compounds as shown in Table 2, synthesized in the same manner as in Preparation Example 5 or 6, were used instead of the hydrazone compound used in Example 18 and the titanium oxyphthalocyanine dye used in Example 18 was used for the carrier generation layer, and their sensitivities are shown in Table 2.

TABLE 2

| Example | Exemplary Compound No. | Sensitivity $(\mu W/cm^2)^{-1}$ |
| --- | --- | --- |
| 20 | 2-1 | 2.1 |
| 21 | 2-3 | 2.0 |
| 22 | 2-12 | 1.7 |
| 23 | 2-15 | 2.3 |
| 24 | 2-19 | 1.3 |

TABLE 2-continued

| Example | Exemplary Compound No. | Sensitivity $(\mu W/cm^2)^{-1}$ |
| --- | --- | --- |
| 25 | 2-25 | 1.6 |

PREPARATION EXAMPLE 7

2.5 g of bis[m-N,N-diethylamino)phenoxy]methane as shown below was dissolved in 52 ml of N,N-dimethylformamide, and 1.7 ml of phosphorous oxychloride was added thereto, and then the reaction was conducted at 60° C. for 4 hours.

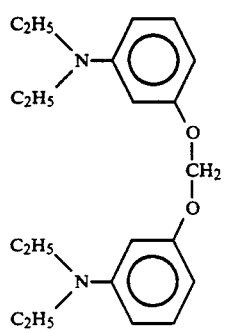

The reaction solution was left to cool and then poured in 200 g of ice water, hydrolyzed with sodium hydroxide, and then subjected to filtration and purification treatments by known methods to obtain 2.5 g of a bisformyl compound as a yellow solid.

This compound was found to be a compound of the following formula from the following values of elemental analysis, the mass spectrometric analysis and the infrared absorption spectrum analysis:

| Elemental analysis: As $C_{23}H_{30}N_2O_4$ | | | |
| --- | --- | --- | --- |
| | C % | H % | N % |
| Calculated | 69.32 | 7.59 | 7.03 |
| Found | 69.23 | 7.71 | 7.13 |
| Results of mass spectrometric analysis: As $C_{23}H_{30}N_2O_4$ | | | |
| MW = 398 | | | |

-continued $M^+ = 398$

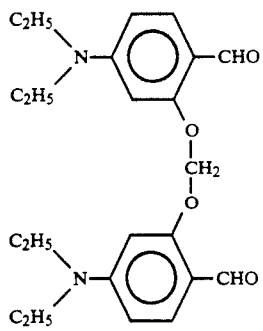

PREPARATION EXAMPLE 8

2.5 g of diformyl compound synthesized in Preparation Example 7 was reacted with 3.2 g of 1,1-diphenylhydrazine in the presence of an acetic acid catalyst in a mixed solution of 30 ml of tetrahydrofuran and 30 ml of methanol at room temperature for 12 hours.

Then, the reaction solution was poured in 500 ml of methanol and further subjected to filtration and purification treatments by known methods to obtain 2.9 g of yellow crystals (melting point: 195° C.).

Figure 5:
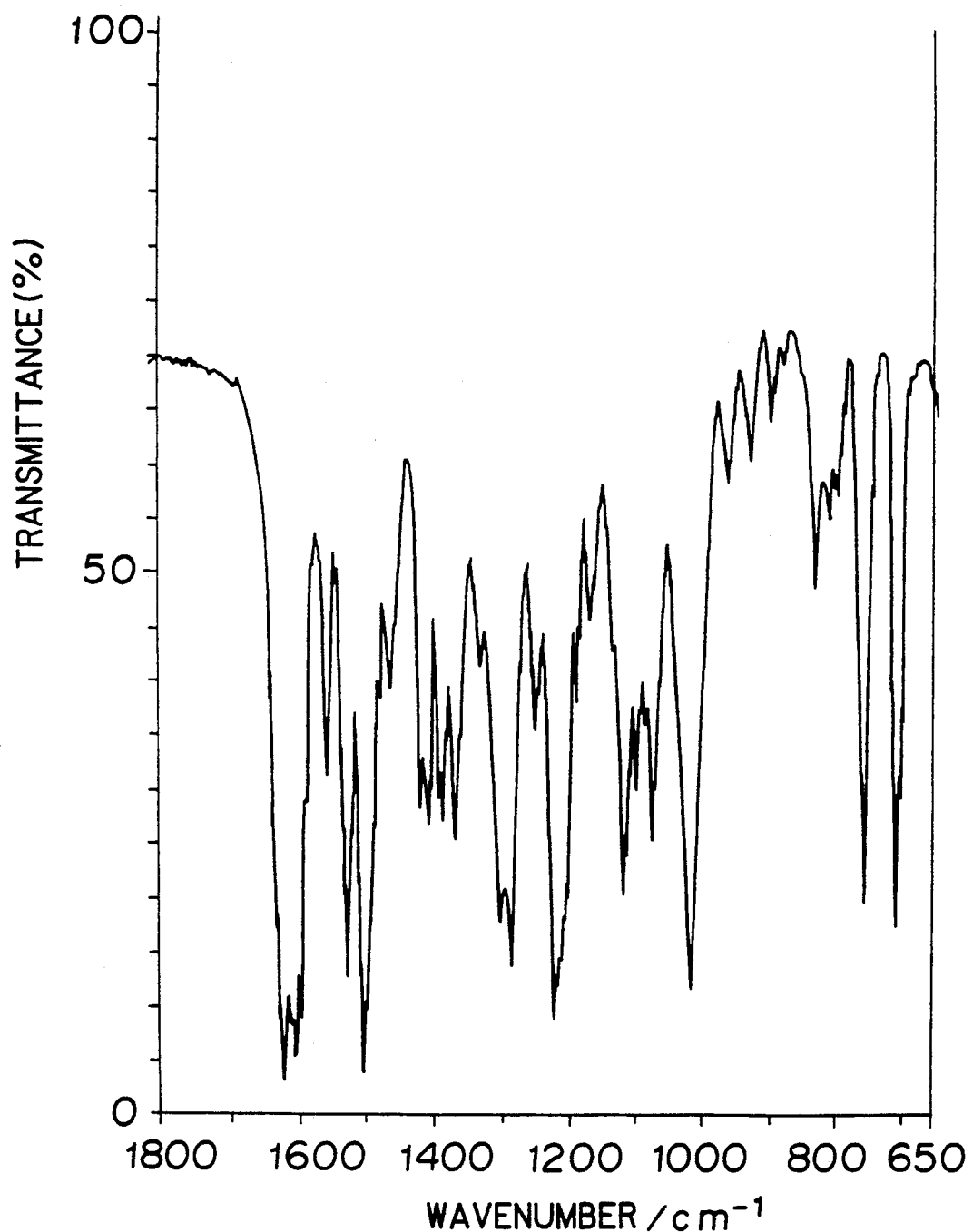
FIG. 5 is an infrared absorption spectrum of the dihydrazone compound obtained in Preparation Example 8.

This compound was found to be a dihydrazone compound of the formula of Exemplary Compound No. 3-1 as mentioned above from the following values of elemental analysis, the mass spectrometric analysis and the infrared absorption spectrum analysis (FIG. 5):

| | Elemental analysis: As $C_{47}H_{50}N_6O_2$ | | |
|---|---|---|---|
| | C % | H % | N % |
| Calculated | 77.23 | 6.89 | 11.50 |
| Found | 77.15 | 6.97 | 11.59 |

| Results of mass spectrometric analysis: As $C_{47}H_{50}N_6O_2$ |
|---|
| MW = 730 |
| $M^+$ = 730 |

EXAMPLE 26

1.0 part of titanium oxyphthalocyanine dye and 0.5 part of polyvinylbutyral (tradename: Polyvinylbutyral #6000, manufactured by Denki Kagaku Kogyo K. K.) were dispersed and pulverized in 30 parts of 4-methoxy-4-methylpentanone-2 (manufactured by Mitsubishi Kasei Corporation).

This dispersion was coated by a wire bar on an aluminium layer vapor-deposited on a polyester film having a thickness of 100 μm so that the weight after drying would be 0.2 g/m², followed by drying to form a carrier generation layer.

A coating solution prepared by dissolving 70 parts of the hydrazone compound prepared in Preparation Example 8 and 100 parts of polycarbonate resin as shown below (molecular weight: about 10,000 to 40,000) in 900 parts of dioxane, was coated thereon and dried to form a carrier transport layer having a thickness of 17 μm.

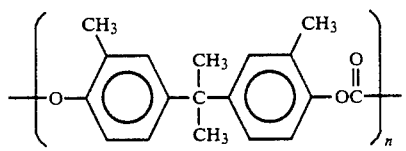

With respect to the electrophotographic photoreceptor having a photosensitive layer comprising two layers thus obtained, the sensitivity i.e. the half-decay exposure intensity was measured and found to be 2.0 $(\mu W/cm^2)^{-1}$.

Here, the half-decay exposure intensity was determined by firstly charging the photoreceptor in a dark place with corona discharge at −4.8 KV, then subjecting to exposure to a light of 775 nm, and measuring the exposure intensity required until the surface potential decayed from 500 V to 250 V.

EXAMPLE 27

A photoreceptor was produced in the same manner as in Example 26 except that an unsymmetrical disazo dye of the following formula was used instead of the phthalocyanine dye used in Example 26. The photoreceptor was exposed to incandescent light, and the half-decay exposure intensity was measured to be 1.5 lux.sec.

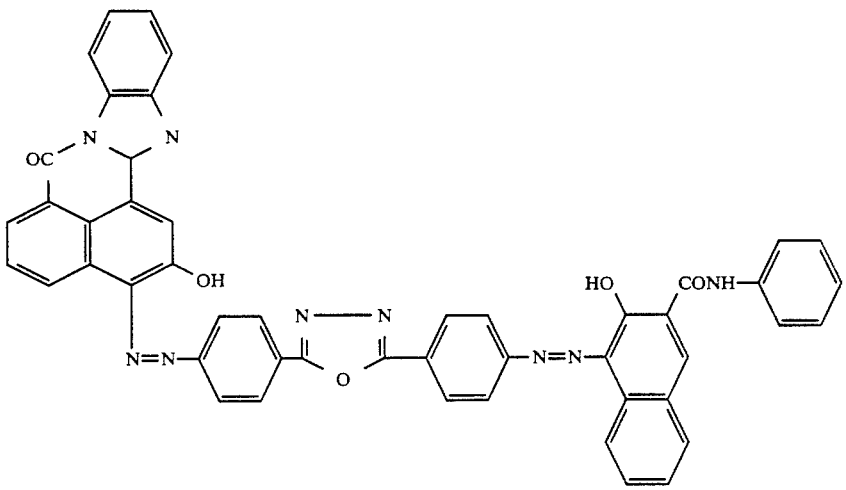

EXAMPLES 28 TO 36

Electrophotographic photoreceptors were produced in the same manner as in Example 26 except that dihydrazone compounds as shown in the following Table 3, synthesized in the same manner as in Preparation Example 8, were used instead of the hydrazone compound used in Example 26, and the titanium oxyphthalocyanine dye used in Example 26 was used for the carrier generation layer, and their sensitivities are shown in Table 3.

TABLE 3

| Example | Exemplary Compound No. | Sensitivity $(\mu W/cm^2)^{-1}$ |
|---------|------------------------|-------------------------------|
| 28 | 3-1 | 2.0 |
| 29 | 3-2 | 2.1 |
| 30 | 3-4 | 1.8 |
| 31 | 3-7 | 2.1 |
| 32 | 3-8 | 2.3 |
| 33 | 3-12 | 1.6 |
| 34 | 3-14 | 1.9 |
| 35 | 3-15 | 1.7 |
| 36 | 3-19 | 1.7 |

We claim:

1. An electrophotographic photoreceptor comprising an electrically conductive support and a photosensitive layer formed thereon, wherein said photosensitive layer contains at least one member selected from the group consisting of hydrazone compounds of the formulas (I), (II) and (III):

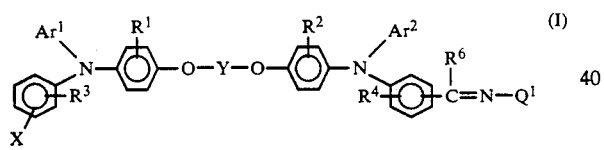  (I)

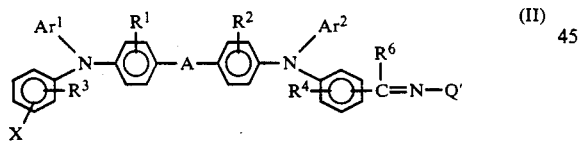  (II)

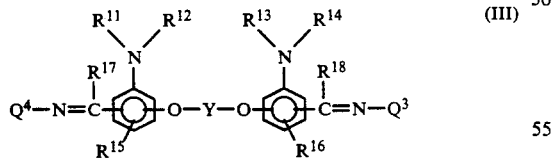  (III)

wherein X is a hydrogen atom or a group of the formula (IV):

  (IV)

$Q^1$ is a group of the formula (V), (VI), (VII), (VIII) or (IX); $Q^2$ is a group of the formula (VI), (VII), (VIII), (IX) or (X); each of $Q^3$ and $Q^4$ which may be the same or different, is a group of the formula (VI), (VII), (VIII), (IX) or (XI):

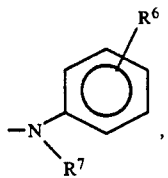  (V)

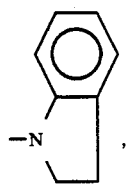  (VI)

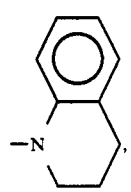  (VII)

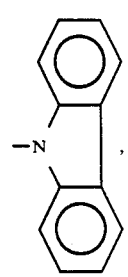  (VIII)

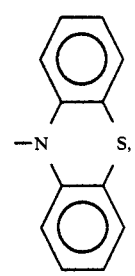  (IX)

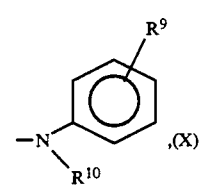  (X)

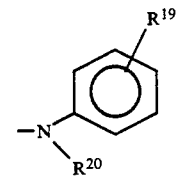  (XI)

Y is a bivalent hydrocarbon group which may have substituents, A is an aliphatic linking group which may have substituents, where the main chain of the linking group may contain an oxygen atom or a carbon-carbon double bond; in the case where the main chain of the linking group is composed of only carbon atoms, the constituting carbon number is from 3 to 5; and in the case where the oxygen atom is contained, the constituting carbon-carbon chain length has the carbon number of from 2 to 5; each of $Ar^1$ and $Ar^2$ which may be the same or different, is an aryl group which may have substituents or a heterocyclic group; each of $R^1$, $R^2$, $R^3$, $R^4$, $R^5$, $R^9$, $R^{15}$, $R^{16}$ and $R^{19}$ which may be the same or different, is a hydrogen atom, a lower alkyl group which may have substituents, a halogen atom or a lower alkoxy group which may have substituents; each of $R^6$, $R^8$, $R^{17}$ and $R^{18}$ which may be the same or different, is a hydrogen atom, a methyl group or a phenyl group which may have substituents; each of $R^7$ and $R^{10}$ is an aryl group which may have substituents in the formula (I), or an aryl group which may have substituents or a heterocyclic group in the formula (II); each of $R^{11}$, $R^{12}$, $R^{13}$ and $R^{14}$ which may be the same or different, is an alkyl group which may have substituents, an aralkyl group which may have substituents; an aryl group which may have substituents, a vinyl group which may have substituents, or an allyl group; and $R^{20}$ is an aryl group which may have substituents, or a heterocyclic group.

2. The electrophotographic photoreceptor according to claim 1, wherein the photosensitive layer contains the hydrazone compound of the formula (I).

3. The electrophotographic photoreceptor according to claim 1, wherein the photosensitive layer contains the hydrazone compound of the formula (II).

4. The electrophotographic photoreceptor according to claim 1, wherein the photosensitive compound contains the hydrazone compound of the formula (III).

5. The electrophotographic photoreceptor according to claim 1, wherein the photosensitive layer comprises a carrier generation layer and a carrier transport layer contains at least one member selected from the group consisting of the hydrazone compounds of the formulas (I), (II) and (III).

6. The electrophotographic photoreceptor according to claim 5, wherein the carrier transport layer contains at least one member selected from the group consisting of the hydrazone compounds of the formulas (I), (II) and (III), and a binder.

7. The electrophotographic photoreceptor according to claim 1, wherein the photosensitive layer contains photoconductive particles capable of generating an electric charge carrier and at least one member selected from the group consisting of the hydrazone compounds of the formulas (I), (II) and (III), which are added in a binder.

8. The electrophotographic photoreceptor according to claim 2, wherein X is a hydrogen atom.

9. The electrophotographic photoreceptor according to claim 2, wherein X is a group of the formula (IV).

10. The electrophotographic photoreceptor according to claim 3, wherein X is a hydrogen atom.

11. The electrophotographic photoreceptor according to claim 3, wherein X is a group of the formula (IV).

12. The electrophotographic photoreceptor according to claim 4, wherein X is a hydrogen atom.

13. The electrophotographic photoreceptor according to claim 4, wherein X is a group of the formula (IV).

* * * * *